(12) United States Patent
Lo

(10) Patent No.: US 12,283,050 B2
(45) Date of Patent: *Apr. 22, 2025

(54) SYSTEMS AND METHODS FOR DISPLAYING AUGMENTED ANATOMICAL FEATURES

(71) Applicant: Gustav Lo, Petoskey, MI (US)

(72) Inventor: Gustav Lo, Petoskey, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/455,200

(22) Filed: Aug. 24, 2023

(65) Prior Publication Data

US 2023/0401713 A1 Dec. 14, 2023

Related U.S. Application Data

(63) Continuation of application No. 17/672,932, filed on Feb. 16, 2022, now Pat. No. 11,741,609, which is a
(Continued)

(51) Int. Cl.
G06T 7/00 (2017.01)
G06T 7/73 (2017.01)
(Continued)

(52) U.S. Cl.
CPC .............. G06T 7/0014 (2013.01); G06T 7/74 (2017.01); G06T 19/006 (2013.01); G06T 19/20 (2013.01);
(Continued)

(58) Field of Classification Search
None
See application file for complete search history.

(56) References Cited

U.S. PATENT DOCUMENTS 6,301,495 B1 10/2001 Gueziec
9,105,207 B2 8/2015 Leung
(Continued)

FOREIGN PATENT DOCUMENTS

CN 105788390 A 7/2016
CN 206431875 U 8/2017
(Continued)

OTHER PUBLICATIONS

WIPO, International Search Report and Written Opinion for PCT Application No. PCT/2021/052274, mailed Jan. 11, 2022.
(Continued)

Primary Examiner — Tapas Mazumder
(74) Attorney, Agent, or Firm — Miller Johnson

(57) ABSTRACT

A method, user device, and system for displaying augmented anatomical features is disclosed. The method includes detecting a target individual, displaying a visual representation of the body, and determining an anatomical profile of the target individual based on a plurality of reference markers. The method further includes displaying, on the display, a graphical representation of the inner anatomical features onto the visual representation of the body so as to assist in the identification of the inner anatomical features. In another aspect, an initial three-dimensional representation of the body is mapped and a preferred anatomical profile is determined based upon the reference markers. The initial three-dimensional representation of the body is modified to be the shape of the preferred anatomical profile and displayed.

19 Claims, 16 Drawing Sheets

Related U.S. Application Data continuation of application No. 17/062,085, filed on Oct. 2, 2020, now Pat. No. 11,288,802, which is a continuation-in-part of application No. 16/514,163, filed on Jul. 17, 2019, now Pat. No. 10,832,486.

(51) Int. Cl.
*G06T 19/00* (2011.01)
*G06T 19/20* (2011.01)

(52) U.S. Cl.
CPC .......... *G06T 2207/30008* (2013.01); *G06T 2207/30052* (2013.01); *G06T 2207/30204* (2013.01); *G06T 2219/2021* (2013.01)

(56) References Cited

U.S. PATENT DOCUMENTS

| | | | |
|---|---|---|---|
| 9,123,155 | B2 | 9/2015 | Cunningham et al. |
| 9,547,940 | B1 | 1/2017 | Sun et al. |
| 10,010,379 | B1 | 7/2018 | Gibby et al. |
| 10,154,823 | B2 | 12/2018 | Von Berg et al. |
| 10,194,990 | B2 | 2/2019 | Amanatullah et al. |
| 2009/0220136 | A1 | 9/2009 | Bova |
| 2011/0313479 | A1 | 12/2011 | Rubin |
| 2013/0038707 | A1 | 2/2013 | Cunningham et al. |
| 2013/0293578 | A1 | 11/2013 | Leung |
| 2013/0325493 | A1 | 12/2013 | Wong et al. |
| 2014/0275760 | A1* | 9/2014 | Lee .............. A61B 1/00045 600/102 |
| 2016/0135925 | A1 | 5/2016 | Mason et al. |
| 2016/0225192 | A1 | 8/2016 | Jones et al. |
| 2016/0324580 | A1 | 11/2016 | Esterberg |
| 2016/0370239 | A1 | 12/2016 | Cummings |
| 2017/0090675 | A1 | 3/2017 | Lee et al. |
| 2017/0252108 | A1 | 9/2017 | Rios et al. |
| 2017/0367771 | A1 | 12/2017 | Tako et al. |
| 2018/0012413 | A1 | 1/2018 | Jones et al. |
| 2018/0012416 | A1 | 1/2018 | Jones et al. |
| 2018/0140362 | A1 | 5/2018 | Cali et al. |
| 2018/0192964 | A1 | 7/2018 | Stalder et al. |
| 2018/0286136 | A1 | 10/2018 | Jones et al. |
| 2018/0293802 | A1 | 10/2018 | Hendricks et al. |
| 2019/0024508 | A1 | 1/2019 | Hussey |
| 2019/0069871 | A1 | 3/2019 | Tkaczyk et al. |
| 2019/0080515 | A1 | 3/2019 | Geri et al. |
| 2019/0206134 | A1 | 7/2019 | Devam et al. |
| 2019/0240508 | A1 | 8/2019 | Friman et al. |
| 2019/0282324 | A1* | 9/2019 | Freeman .............. A61H 31/005 |
| 2019/0333274 | A1 | 10/2019 | Brown |
| 2019/0365498 | A1 | 12/2019 | Gibby et al. |
| 2020/0246081 | A1 | 8/2020 | Johnson et al. |
| 2020/0305795 | A1* | 10/2020 | Floyd .................. A61B 5/6814 |
| 2021/0027469 | A1 | 1/2021 | Lo |

FOREIGN PATENT DOCUMENTS

| | | |
|---|---|---|
| CN | 107536643 A | 1/2018 |
| EP | 3423972 A1 | 1/2019 |
| JP | 2018022426 A | 2/2018 |
| JP | 2019087279 A | 6/2019 |
| WO | 02080773 A1 | 10/2002 |
| WO | 2013165408 A1 | 11/2013 |
| WO | 2014030262 A1 | 2/2014 |
| WO | 2015145395 A1 | 10/2015 |
| WO | 2016140989 A1 | 9/2016 |
| WO | 2016162789 A2 | 10/2016 |
| WO | 2016184704 A1 | 11/2016 |
| WO | 2017151963 A1 | 9/2017 |
| WO | 2017165301 A1 | 9/2017 |
| WO | 2018156633 A1 | 8/2018 |
| WO | 2018162079 A1 | 9/2018 |
| WO | 2018165767 A1 | 9/2018 |
| WO | 2018195529 A1 | 10/2018 |
| WO | 2019053627 A1 | 3/2019 |

OTHER PUBLICATIONS

Christine A. Campisi et al., 'Augmented Reality in Medical Education and Training: From Physicians to Patients', In: Augmented Reality in Education, pp. 111-138, May 27, 2020.

WIPO, International Search Report and Written Opinion, dated Oct. 26, 2020, related to International Application No. PCT/US2020/042042.

European Patent Office, Supplemental European Search Report for EP application No. 20840697, dated Jul. 5, 2023.

Meng, "Personalized Perception and Interaction with Medical Information in Mixed Reality Environments", Technische Universität München.

De Belen et al., "A systematic review of the current state of collaborative mixed reality technologies: 2013-2018".

Japanese Patent Office, Reasons for Rejection for JP app. No. 2022-135107, dated Aug. 31, 2023.

USPTO, Non-Final Office Action mailed Oct. 27, 2022 related to U.S. Appl. No. 17/672,932.

USPTO, Notice of Allowance mailed Aug. 30, 2023 related to U.S. Appl. No. 17/672,932.

USPTO, Notice of Allowance mailed Apr. 12, 2023, related to U.S. Appl. No. 17/672,932.

USPTO, Non-Final Office Action mailed Oct. 16, 2019 related to U.S. Appl. No. 16/514,163.

USPTO, Non-Final Office Action mailed Jul. 26, 2021, related to U.S. Appl. No. 17/062,085.

USPTO, Notice of Allowance mailed Jul. 7, 2020 related to U.S. Appl. No. 16/514,163.

USPTO, Corrected Notice of Allowability mailed Feb. 9, 2022 related to U.S. Appl. No. 17/062,085.

USPTO, Final Office Action mailed Apr. 9, 2020 related to U.S. Appl. No. 16/514,163.

Japanese Office Action mailed Jun. 13, 2024 for JP2023518068, 9 pages.

Canadian Patent Office, Canadian Office Action regarding Canadian Application No. 3,147,594, dated Jan. 2, 2025, 5 pages.

* cited by examiner

SYSTEMS AND METHODS FOR DISPLAYING AUGMENTED ANATOMICAL FEATURES

CROSS-REFERENCE TO RELATED APPLICATIONS

This application is a continuation of U.S. application Ser. No. 17/672,932 filed on Feb. 16, 2022, which is a continuation of U.S. application Ser. No. 17/062,085, now U.S. Pat. No. 11,288,802, filed on Oct. 2, 2020, which is a continuation-in-part of U.S. application Ser. No. 16/514,163, now U.S. Pat. No. 10,832,486, filed on Jul. 17, 2019. The entire contents of the above applications are incorporated herein by reference.

TECHNICAL FIELD

This disclosure relates generally to a method, system and user device for displaying inner anatomical features.

BACKGROUND

This section provides background information related to the present disclosure and is not necessarily prior art.

Augmented reality technology has the ability to alter, or augment, a user's view of the surrounding environment by overlaying computer-generated images onto the user's view of the real world, creating a composite view consisting of both real and virtual elements. Augmented reality offers the user an enriching experience by augmenting, via overlaid digital content, the user's perception of their environment and their immediate surroundings. The user may augment their view through various electronic devices, such as wearable technology (e.g., headsets, glasses, smart watches, etc.), tablets, laptops, mobile devices, or other devices. The user can use these electronic devices to augment their perception of their environment by overlaying, for instance, information about their surroundings, or graphical images to enhance their perception of their current environment.

Augmented reality can be used in a variety of environments by a variety of users to educate each user about their surroundings. For example, a railyard worker can wear augmented reality glasses that allow them to view information about trains in the railyard, or a biologist may use augmented reality to identify different species of plants surrounding them.

Healthcare professionals, such as doctors and nurses, are in continuous need of technological assistance in order to treat their patients. Particularly, healthcare professionals constantly need to obtain and accumulate data on their patients in order to assess the best treatment plan for the patient. Healthcare professionals would greatly benefit from using augmented reality to gather data on their patients. While known augmented reality technology has been used for healthcare professionals to gather patient data, a continuous need for improvement remains in the pertinent art.

SUMMARY

This section provides a general summary of the disclosure, and is not a comprehensive disclosure of its full scope or all of its features.

The instant disclosure provides various methods, user devices, and systems for displaying augmented anatomical features. One aspect of the disclosure provides a method. The method includes detecting a target individual. The target individual has a body. The method further includes tracking the target individual. The method further includes displaying, on a display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of anatomical features. The method further includes displaying, on the display, graphical representations of the anatomical features overlaid on the visual representation of the body. The graphical representations of the anatomical features are oriented on the visual representation of the body based on the anatomical profile.

Implementations of the disclosure may also include one or more of the following features. In some implementations, the plurality of reference markers correspond to at least one of a navel, a portion of a sternum, a portion of a hip, a portion of a collarbone, or a portion of a shoulder.

In some implementations, the anatomical profile of the target individual is further based on a plurality of data corresponding to the body.

In some implementations, the plurality of anatomical features includes at least one of organs, bones, muscles, or blood vessels.

In some implementations, the plurality of reference markers are identified by a user interacting with the display.

In some implementations, the anatomical profile of the target individual includes a default anatomical profile that is modified based on the plurality of reference markers.

According to another aspect of the disclosure, a user device is provided. The user device includes a display. The user device further includes data processing hardware in communication with the display. The user device further includes memory hardware in communication with the data processing hardware. The memory hardware stores instructions that when executed on the data processing hardware cause the data processing hardware to perform operations. According to this aspect, the operations carry out a method. The method includes detecting a target individual. The target individual has a body. The method further includes tracking the target individual. The method further includes displaying, on the display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of anatomical features. The method further includes displaying, on the display, graphical representations of the anatomical features overlaid on the visual representation of the body. The graphical representations of the anatomical features are oriented on the visual representation of the body based on the anatomical profile.

This aspect may also include one or more of the following features. In some implementations, the plurality of reference markers correspond to at least one of a navel, a portion of a sternum, a portion of a hip, a portion of a collarbone, or a portion of a shoulder.

In some implementations, the anatomical profile of the target individual is further based on a plurality of data corresponding to the body.

In some implementations, the plurality of anatomical features includes at least one of organs, bones, muscles, or blood vessels.

In some implementations, the plurality of reference markers are identified by a user interacting with the display.

In some implementations, the anatomical profile of the target individual includes a default anatomical profile that is modified based on the plurality of reference markers.

According to another aspect of the disclosure, a system is provided. The system includes a user device. The user device includes a first display. The user device further includes data processing hardware in communication with the first display. The user device further includes memory hardware in communication with the data processing hardware. The memory hardware stores instructions that when executed on the data processing hardware cause the data processing hardware to perform operations. According to this aspect, the operations carry out a method. The method includes, detecting a target individual. The target individual has a body. The method further includes tracking the target individual. The method further includes displaying, on the first display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of anatomical features. The method further includes displaying, on the first display, graphical representations of the anatomical features overlaid on the visual representation of the body. The graphical representations of the anatomical features are oriented on the visual representation of the body based on the anatomical profile. The system further includes a wearable in communication with the user device. The wearable includes a second display configured to display graphical representations of the anatomical features overlaid on the visual representation of the body. The graphical representations of the anatomical features are oriented on the visual representation of the body based on the anatomical profile.

This aspect may also include one or more of the following features. In some implementations, the plurality of reference markers correspond to at least one of a navel, a portion of a sternum, a portion of a hip, a portion of a collarbone, or a portion of a shoulder.

In some implementations, the anatomical profile of the target individual is further based on a plurality of data corresponding to the body.

In some implementations, the plurality of anatomical features includes at least one of organs, bones, muscles, or blood vessels.

In some implementations, the plurality of reference markers are identified by a user interacting with the display.

In some implementations, the wearable is further configured to detect and track the target individual independently of the user device.

In some implementations, the anatomical profile of the target individual includes a default anatomical profile that is modified based on the plurality of reference markers.

According to another aspect of the disclosure, a method is provided. The method includes detecting a target individual. The target individual has a body. The method further includes displaying, on a display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of inner anatomical features. The method further includes selecting a medical procedure. The method further includes determining a future state anatomical profile corresponding to the selected medical procedure. The method further includes displaying, on the display, graphical representations of the visual representation of the body modified with the inner anatomical features based on the selected medical procedure.

According to another aspect of the disclosure, a method is provided. The method includes detecting a target individual. The target individual has a body. The method further includes displaying, on a display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of inner anatomical features. The method further includes displaying, on the display, a graphical representation of the inner anatomical features onto the visual representation of the body so as to assist in the identification of the inner anatomical features.

Implementations of the disclosure may also include one or more of the following features. In some implementations, the plurality of reference markers correspond to at least one of a navel, a portion of a sternum, a portion of a hip, a portion of a collarbone, a portion of a shoulder, nose, corner of the eyes, tips of the ears, chin and the like.

In some implementations, the anatomical profile of the target individual is further based on a plurality of data corresponding to the body.

In some implementations, the plurality of anatomical features includes at least one of organs, bones or muscles.

In some implementations, the plurality of reference markers are identified by a user interacting with the display.

In some implementations, the method further includes the step of selecting a medical procedure and determining a future state anatomical profile corresponding to the selected medical procedure, wherein the graphical representation includes a visual representation of the body modified with the inner anatomical features based on the selected medical procedure. In such an implementation, the graphical representation of the body may be modified with outer anatomical features based on the selected medical procedure. In such an implementation, the method further includes providing a graphical representation of the body modified with outer anatomical features based on the selected medical procedure. In such an implementation, the selected medical procedure is a procedure effecting at least one of organs, bones or muscles. In such an implementation, the plurality of reference markers correspond to a body structure such as a navel, a portion of a sternum, a portion of a hip, a portion of a collarbone, a portion of a shoulder, lips, corners of the mouth, tip of the nose, or ears. In such an implementation, the anatomical profile of the target individual may be further based on a plurality of data corresponding to the body. In such an implementation, the plurality of reference markers may be identified by a user interacting with the display.

In some implementation, the method may include the step of identifying at least one of a disease, an inherited condition or an anatomical variant and determining an anatomical profile corresponding to the plurality of reference markers and at least one of the identified disease, the identified inherited condition or the identified anatomical variant, wherein the graphical representation includes a visual representation of the body modified with the inner anatomical features based on the determined anatomical profile. In such an implementation, the disease, the inherited condition and the anatomical variant effects at least one of organs, bones or muscles. In such an implementation, the plurality of reference markers may correspond to at least one of a navel, a portion of a sternum, a portion of a hip, a portion of a collarbone, a portion of a shoulder, lips, corners of the mouth, tip of the nose, or ears. In such an implementation, the anatomical profile of the target individual may be further based on a plurality of data corresponding to the body. In such an implementation, the plurality of inner anatomical features may include at least one of organs, bones or muscles. In such an implementation, the plurality of reference markers may be identified by a user interacting with the display.

According to another aspect of the disclosure, a user device is provided. The user device includes a display. The user device further includes data processing hardware in communication with the display. The user device further includes memory hardware in communication with the data processing hardware. The memory hardware stores instructions that when executed on the data processing hardware cause the data processing hardware to perform operations. According to this aspect, the operations carry out a method. The method includes detecting a target individual. The target individual has a body. The method further includes displaying, on the display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of inner anatomical features. The method further includes displaying, on the display, a graphical representation of the inner anatomical features onto the visual representation of the body so as to assist in the identification of the inner anatomical features.

This aspect may also include one or more of the following features. In some implementations, the plurality of reference markers correspond to at least one of a navel, a portion of a sternum, a portion of a hip, a portion of a collarbone, or a portion of a shoulder, lips, corners of the mouth, tip of the nose, or ears.

In some implementations, the anatomical profile of the target individual is further based on a plurality of data corresponding to the body.

In some implementations, the plurality of anatomical features includes at least one of organs, bones or muscles.

In some implementations, the plurality of reference markers are identified by a user interacting with the display.

In some implementations, the plurality of reference markers are identified by the data processing hardware.

In some implementations, the anatomical profile of the target individual includes a default anatomical profile that is modified based on the plurality of reference markers.

In some implementations, the operations further include selecting a medical procedure and determining a future state anatomical profile corresponding to the selected medical procedure, wherein the graphical representation includes a visual representation of the body modified with the inner anatomical features based on the selected medical procedure. In such an implementation, the selected medical procedure is a procedure at least one of organs, bones or muscles.

In some implementations, the operations further identify at least one of a disease, an inherited condition or an anatomical variant and determining an anatomical profile corresponding to the plurality of reference markers and at least one of the identified disease, the identified inherited condition or the identified anatomical variant, wherein the graphical representation includes a visual representation of the body modified with the inner anatomical features based on the determined anatomical profile. In such an implementation, the disease, the inherited condition and the anatomical variant effects at least one of organs, bones or muscles. In such an implementation, the plurality of reference markers may correspond to at least one of a navel, a portion of a sternum, a portion of a hip, a portion of a collarbone, a portion of a shoulder, lips, corners of the mouth, tip of the nose, or ears. In such an implementation, the anatomical profile of the target individual may be further based on a plurality of data corresponding to the body. In such an implementation, the plurality of inner anatomical features may include at least one of organs, bones or muscles. In such an implementation, the plurality of reference markers may be identified by a user interacting with the display.

According to another aspect of the disclosure, a system is provided. The system includes a user device. The user device includes a first display. The user device further includes data processing hardware in communication with the first display. The user device further includes memory hardware in communication with the data processing hardware. The memory hardware stores instructions that when executed on the data processing hardware cause the data processing hardware to perform operations. According to this aspect, the operations carry out a method. The method includes, detecting a target individual. The target individual has a body. The method further includes displaying, on the first display, a visual representation of the body. The method further includes identifying a plurality of reference markers on the visual representation of the body. The method further includes determining, at a processor, an anatomical profile of the target individual. The anatomical profile of the target individual is determined based on the plurality of reference markers. The anatomical profile includes a plurality of inner anatomical features. The system further includes a wearable in communication with the user device. The wearable includes a second display configured to display a graphical representation of the inner anatomical features onto the visual representation of the body so as to assist in the identification of the inner anatomical features.

This aspect may also include one or more of the following features. In some implementations, the plurality of reference markers correspond to at least one of a navel, a portion of a sternum, a portion of a hip, a portion of a collarbone, or a portion of a shoulder.

In some implementations, the anatomical profile of the target individual is further based on a plurality of data corresponding to the body.

In some implementations, the plurality of anatomical includes at least one of organs, bones or muscles.

In some implementations, the plurality of reference markers are identified by a user interacting with the display.

In some implementations, the wearable is further configured to detect and map the target individual independently of the user device.

In some implementations, the selected medical procedure is a procedure effecting at least one of organs, bones or muscles.

In some implementations, the method further includes selecting a medical procedure and determining a future state anatomical profile corresponding to the selected medical procedure, wherein the graphical representation includes a visual representation of the body modified with the inner anatomical features based on the selected medical procedure.

In some implementations, the method further includes identifying at least one of a disease, an inherited condition or an anatomical variant and determining an anatomical profile corresponding to the plurality of reference markers and at least one of the identified disease, the identified inherited condition or the identified anatomical variant, wherein the graphical representation includes a visual representation of the body modified with the inner anatomical features based on the determined anatomical profile. In such an implementation, the disease, the inherited condition and the anatomical variant effects at least one of organs, bones or muscles. In such an implementation, the plurality of reference markers may correspond to at least one of a navel, a portion of a sternum, a portion of a hip, a portion of a collarbone, a portion of a shoulder, lips, corners of the mouth, tip of the nose, or ears. In such an implementation, the anatomical profile of the target individual may be further based on a plurality of data corresponding to the body. In such an implementation, the plurality of inner anatomical features may include at least one of organs, bones or muscles. In such an implementation, the plurality of reference markers may be identified by a user interacting with the display.

According to another aspect of the disclosure, a method is provided. The method includes mapping a target individual. The target individual has a body. The method further generating an initial three-dimensional representation of the body based on the mapping, the three-dimensional representation including a plurality of anatomical features of the body. The method further includes identifying a plurality of reference markers on the visual representation of the body. The method further includes determining, at a processor, a preferred anatomical profile of the target individual. The preferred anatomical profile of the target individual is determined based on the plurality of reference markers. The preferred anatomical profile being a preferred three-dimensional representation of the body. The method includes modifying in three dimensions, at the processor, the initial three-dimensional representation of the body so as to have a shape of the preferred anatomical profile and displaying, on the display, the modified initial three-dimensional representation of the body.

In some implementations, the plurality of reference markers correspond to at least one of a navel, a portion of a sternum, a portion of a hip, a portion of a collarbone, a portion of a shoulder, lips, corners of the mouth, tip of the nose, or ears.

Implementations of the disclosure may also include one or more of the following features. In some implementations, method includes selecting a medical procedure relating to a desired body part; and replacing the desired body part with a corresponding desired body part taken from the preferred anatomical profile so as to generate a future anatomical image and displaying the future anatomical image.

In some implementations, the medical procedure is one selected from the list consisting of a liposuction, a breast enhancement, and a tummy tuck.

In some implementations, the future anatomical image is displayed in three-dimensions.

According to another aspect of the disclosure, a user device is provided. The user device includes a display. The user device further includes data processing hardware in communication with the display. The user device further includes memory hardware in communication with the data processing hardware. The memory hardware stores instructions that when executed on the data processing hardware cause the data processing hardware to perform operations. According to this aspect, the operations carry out a method. The method includes mapping a target individual. The target individual has a body. The method further includes generating an initial three-dimensional representation of the body based on the mapping, the initial three-dimensional representation. The method further includes identifying a plurality of reference markers on the initial three-dimensional representation of the body. The method further includes determining, at a processor, a preferred anatomical profile of the target individual based on the plurality of reference markers, the preferred anatomical profile being a preferred three-dimensional representation of the body and modifying in three dimensions, at the processor, the initial three-dimensional representation of the body so as to have a shape of the preferred anatomical profile. The method further includes displaying, on the display, a graphical representation of the modified initial three-dimensional representation of the body.

In some implementations, the plurality of reference markers correspond to at least one of a navel, a portion of a sternum, a portion of a hip, a portion of a collarbone, a portion of a shoulder, lips, corners of the mouth, tip of the nose, or ears.

Implementations of the disclosure may also include one or more of the following features. In some implementations, method includes selecting a medical procedure relating to a desired body part; and replacing the desired body part with a corresponding desired body part taken from the preferred anatomical profile so as to generate a future anatomical image and displaying the future anatomical image.

In some implementations, the medical procedure is one selected from the list consisting of a liposuction, a breast enhancement, and a tummy tuck.

In some implementations, the future anatomical image is displayed in three-dimensions.

According to another aspect of the disclosure, a system is provided. The system includes a user device. The user device includes a first display. The user device further includes data processing hardware in communication with the first display. The user device further includes memory hardware in communication with the data processing hardware. The memory hardware stores instructions that when executed on the data processing hardware cause the data processing hardware to perform operations. According to this aspect, the operations carry out a method. The method includes, mapping a target individual. The target individual has a body. The method further includes generating an initial three-dimensional representation of the body based on the mapping, the initial three-dimensional representation. The method further includes identifying a plurality of reference markers on the initial three-dimensional representation of the body. The method further includes determining, at a processor, a preferred anatomical profile of the target individual based on the plurality of reference markers, the preferred anatomical profile being a preferred three-dimensional representation of the body. The method further includes modifying in three dimensions, at the processor, the initial three-dimensional representation of the body so as to have a shape of the preferred anatomical profile. The system further includes a wearable in communication with the user device. The wearable includes a second display configured to display a graphical representation of the modified initial three-dimensional representation of the body.

This aspect may also include one or more of the following features. In some implementations, the plurality of reference markers correspond to at least one of a navel, a portion of a sternum, a portion of a hip, a portion of a collarbone, or a portion of a shoulder.

In some implementations, the plurality of reference markers correspond to at least one of a navel, a portion of a sternum, a portion of a hip, a portion of a collarbone, or a portion of a shoulder.

Implementations of the disclosure may also include one or more of the following features. In some implementations, method includes selecting a medical procedure relating to a desired body part; and replacing the desired body part with a corresponding desired body part taken from the preferred anatomical profile so as to generate a future anatomical image and displaying the future anatomical image.

In some implementations, the medical procedure is one selected from the list consisting of a liposuction, a breast enhancement, and a tummy tuck.

In some implementations, the future anatomical image is displayed in three-dimensions. The details of one or more implementations of the disclosure are set forth in the accompanying drawings and the description below. Other aspects, features, and advantages will be apparent from the description and drawings, and from the claims.

DESCRIPTION OF DRAWINGS

The drawings described herein are for illustrative purposes only of selected configurations and not all possible implementations, and are not intended to limit the scope of the present disclosure.

Like reference symbols in the various drawings indicate like elements.

DETAILED DESCRIPTION

Figure 1A:
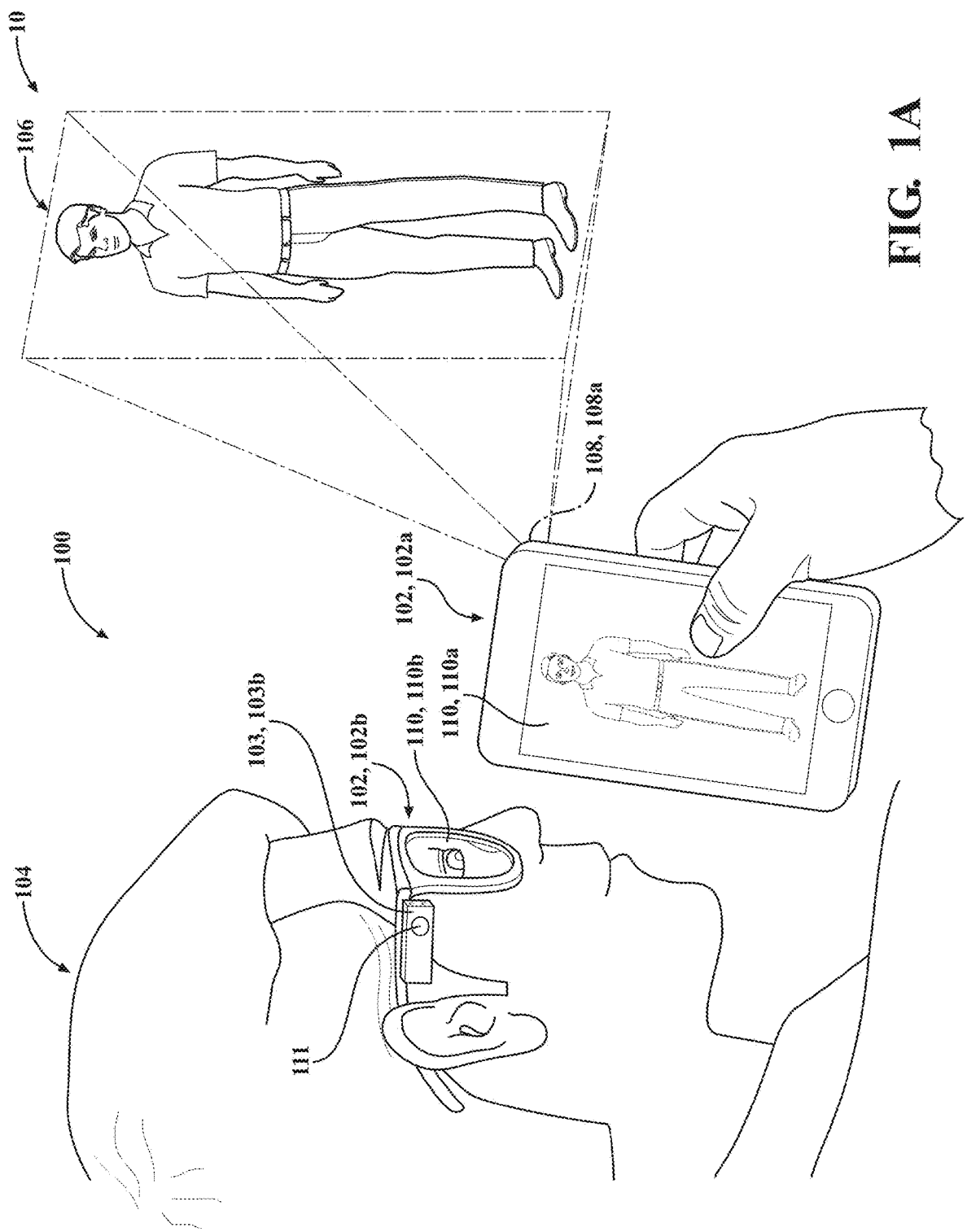
FIG. 1A illustrates an exemplary augmented reality system in accordance with the principles of the present disclosure.

Some of the implementations of the disclosure will be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Example implementations provide methods, user devices, and systems for displaying augmented anatomical features. An augmented reality device, such as an augmented reality headset or other electronic device (e.g., a phone, a tablet computing device, or other computer), may be used to overlay computer-generated or virtual images onto a real world view. Particularly, a healthcare professional, such as a doctor or nurse, may use an augmented reality device to view virtual images of anatomical features of a human body overlaid on a target individual, such as a patient, when the target individual is in view of the healthcare professional. The augmented reality device may project the virtual images onto a display of the augmented reality device such that the virtual images of anatomical features approximate one or more characteristics (e.g., size, location, shape, etc.) of the target individual's actual anatomical features. For example, the augmented reality device may project the virtual images onto a display of the augmented reality device such that the virtual images are located over an approximated appropriate location of the target individual's actual anatomical features according to the anatomy of the target individual. The virtual images may assist a healthcare professional in more accurately assessing a treatment plan or otherwise treating the patient by enhancing the health care professional's visualization of the patient's body.

In another aspect, an augmented reality device, such as a tablet or a mobile device, captures an image of the patient. The augmented reality device may have a software application configured to identify a plurality of reference markers on the image of the patient and determine an anatomical profile of the target individual based on the plurality of reference markers, the anatomical profile including a plurality of inner anatomical features. The software application is further configured to display, on the display, a graphical representation of the inner anatomical features onto the visual representation of the body so as to assist in the identification of the inner anatomical features.

In another aspect, software application includes a list of medical procedures to choose from. The software application may have access to a database populated with a plurality of future state anatomical profiles corresponding to the selected medical procedure, wherein a graphical representation of the future state anatomical profile is overlaid on the image of the patient and modifies the inner anatomical features based on the selected medical procedure. Accordingly, the image capture device displays how the selected medical procedure affects the inner anatomical features of the patient.

In another aspect, the image capture device is configured to map the patient so as to generate an initial three-dimensional representation of the body. The software application may have access to a database that is populated with a plurality of preferred anatomical profiles which correspond to a plurality of reference markers on the initial three-dimensional representation of the patient. The preferred anatomical profile is a profile of a person having a preferred body type. The software application overlays in three dimensions the anatomical features based on the selected medical procedure with the preferred anatomical profile and displays a graphical representation of the preferred three-dimensional representation of the body overlaid on the initial three-dimensional representation of the body. Accordingly, the patient can see what he or she would look like having a preferred body type. As this body is mapped and generated in three-dimensions, the patient can observe the preferred body type in three-dimensions.

Referring now to FIG. 1A, an exemplary augmented reality system 10, including one or more augmented reality device(s) 102, is shown. As will be described in more detail below, a user 104 may use the augmented reality device(s) 102 in a healthcare environment 100 to enhance the user's view of a target individual 106. For example, the user 104 may be a doctor, the target individual 106 may be a patient, and the healthcare environment 100 may be a doctor's office, such that the doctor is able to examine the patient in the doctor's office. In another example, the user 104 may be a paramedic providing emergency treatment to a target individual 106 in a healthcare environment 100 of an ambulance. While the user 104 is generally shown and described herein as being a healthcare professional (e.g., a doctor, nurse, physical therapist or trainer, paramedic, medical assistant, pharmacist, etc.), and the target individual 106 is generally illustrated and described herein as being a healthcare patient, the user 104 or target individual 106 may include various other persons within the scope of the present disclosure. For example, the individual 106 may be an athlete, student, or other individual that has a body and is subject to examination or study by another user 104. In this regard, the augmented reality device(s) 102 may be used in a wide range of settings by a variety of users 104 to examine a target individual 106 in a variety of environments, including the healthcare environment 100.

The augmented reality device 102 may include an image capture device 108 and a display 110. As will be described in more detail below, during use, the image capture device 108 may obtain data about the healthcare environment 100 and, particularly, the target individual 106 located in the healthcare environment 100, and the display 110 may display, for user 104 to view, a composite view of the healthcare environment 100 overlaid with virtual images generated by the augmented reality device 102. In some implementations, the system 10 includes a first augmented reality device 102a and a second augmented reality device 102b. The first augmented reality device 102a may include a smartphone, tablet computer, or other suitable mobile computing device, and the second augmented reality device 102b may include an augmented reality headset. References herein to the augmented reality device 102 will be understood to apply equally to the first augmented reality device 102a and/or the second augmented reality device 102b.

The first augmented reality device 102a may include an image capture device 108a (e.g., a camera) and a display 110a (e.g., a screen). During use, the image capture device 108a may capture images of the healthcare environment 100 and, particularly, the target individual 106. The screen 110a of the first augmented reality device 102a may be used to display a composite view of the healthcare environment 100, captured by the camera 108a, and overlaid with virtual images generated by the first augmented reality device 102a. The first augmented reality device 102a may include a keyboard, mouse, microphone, camera 108a, or touchscreen for allowing user 104 to input data to the first and/or second augmented reality device 102a, 102b.

The second augmented reality device 102b may include an image capture device 108b (e.g., a camera) and a display 110b (e.g., an eyepiece lens). During use, the image capture device 108b may capture images of the healthcare environment and, particularly, the target individual 106. The display 110b may display a composite view of the healthcare environment 100, captured by camera 108b and/or the camera 108a, and overlaid with virtual images generated by the second augmented reality device 102b. The second augmented reality device 102b may include a trackpad 111, camera 108b, microphone, eye tracking device, or gesture tracking device for allowing user 104 to input data to the first and/or second augmented reality device 102a, 102b. For example, the user 104 may input data and otherwise interact with the second augmented reality device 102b by touch via trackpad 111; spoken commands via a microphone; eye gestures via the camera 108b; positional tracking of hands or other body parts via the camera 108b; hand gesture tracking via the camera 108b; or positional tracking of objects such as wands, styluses, pointers, or gloves via the camera 108b.

Though the example shown depicts augmented reality device 102 as a first augmented reality device 102a or second augmented reality device 102b, it should be noted that augmented reality device 102 may be any device (e.g., augmented reality glasses, augmented reality helmet, tablet, etc.) capable of overlaying computer-generated or virtual images onto a real word view.

Figure 1B:
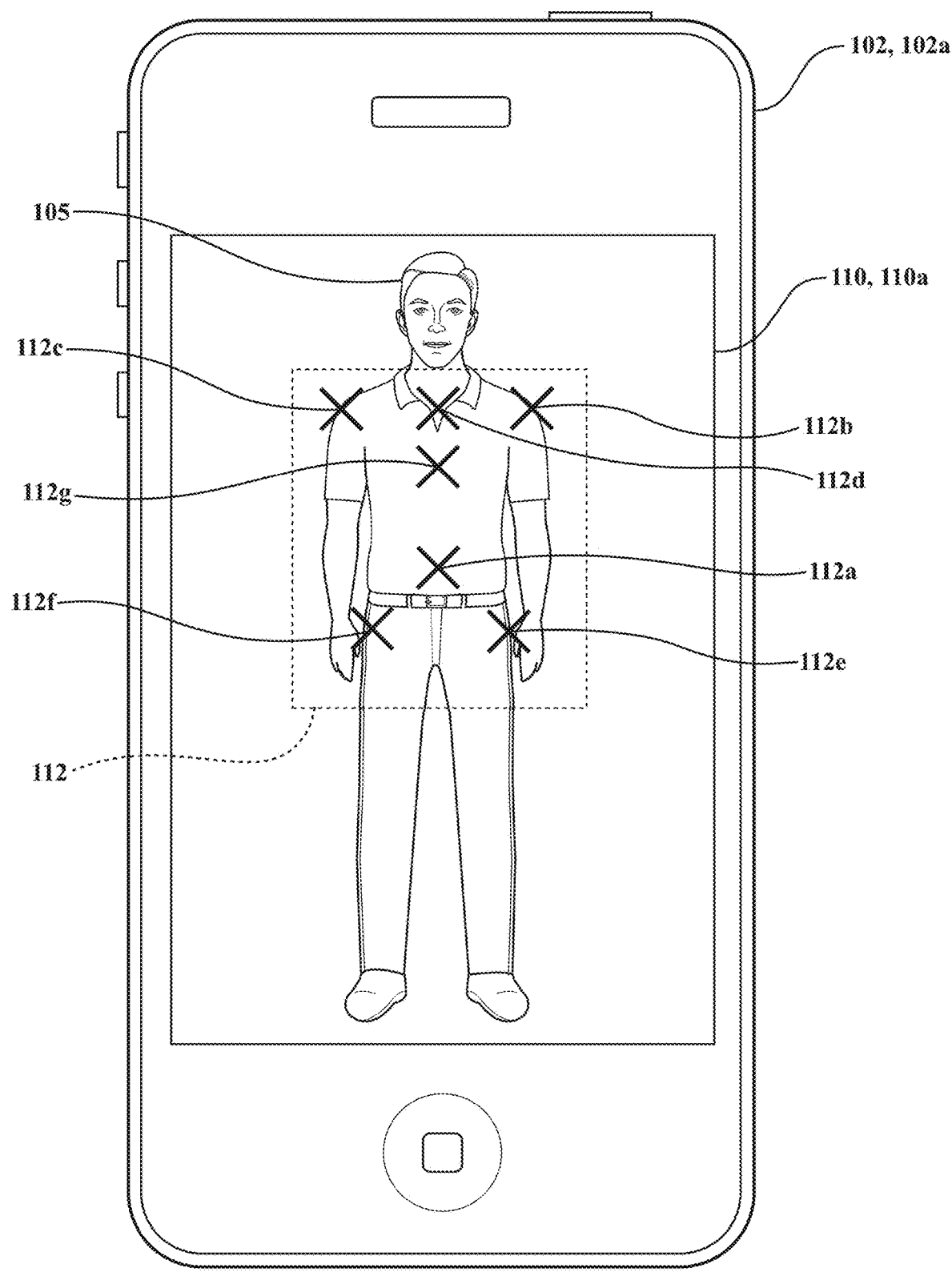
FIG. 1B illustrates an exemplary use of a user device of the augmented reality system of FIG. 1A.

With reference now to FIG. 1B, an exemplary augmented reality device is shown. Although FIG. 1B depicts augmented reality device 102 as the first augmented reality device 102a displaying visual data on screen 110a, it should be noted that, similarly, second augmented reality device 102b may also display visual data on eyepiece display 110b. Augmented reality device 102 may detect the target individual 106 by using image capture device 108. Augmented reality device 102 may then display, on display 110, a visual representation 105 of a body of the target individual 106. In some implementations, the visual representation 105 is a live (e.g., real time) image of the target individual 106. In other implementations, the visual representation 105 is a still image (e.g., a photograph) of the target individual 106. In some implementations, the image capture device 108 includes an infrared camera that uses infrared laser scatter beam technology, for example, to create a three-dimensional visual representation 105 of the target individual 106.

The augmented reality device 102 may identify (e.g., assign) one or more reference markers 112 on the visual representation 105. As described above, in some implementations, the reference markers 112 are identified on a three-dimensional visual representation 105 created using infrared laser scatter beam technology. Each reference marker 112 may correspond to a particular part of, or location on, the body of the target individual 106. In some implementations, the augmented reality device 102 assigns the reference marker(s) 112 by detecting an input (e.g., touch, hand gesture, etc.) from the user 104 corresponding to one or more particular parts of the body of the target individual 106. In particular, the reference markers 112 may be identified by the user's 104 interaction with the augmented reality device 102. For example, in some implementations the user 104 touches the screen 110a at locations corresponding to each reference marker 112. In other implementations, the augmented reality device 102b receives an input from the user 104 via the camera 108b, or the trackpad 111 corresponding to each reference marker 112. For example, the camera 108b may capture the location of the user's 104 hand at locations corresponding to each reference marker 112.

Figure 4:
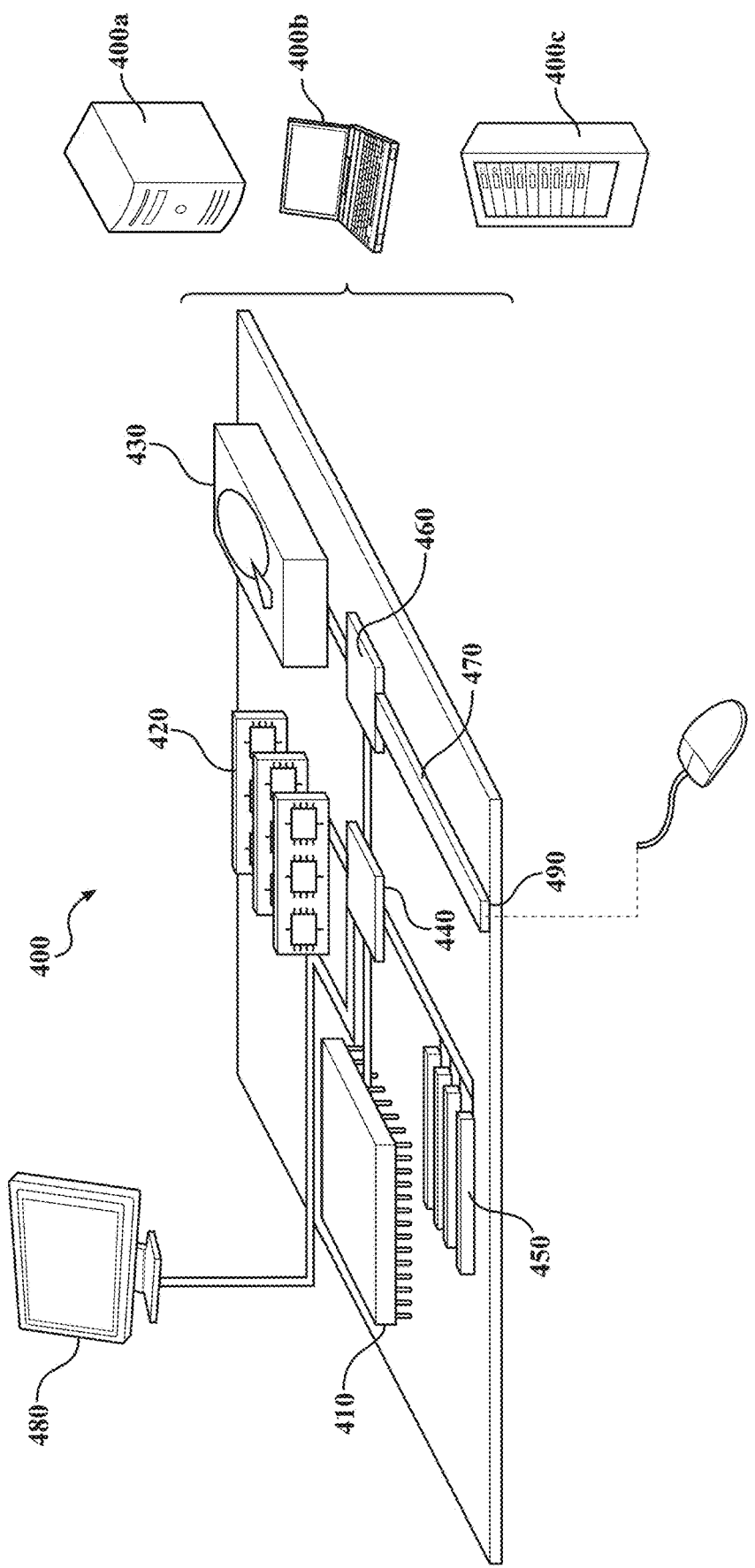
FIG. 4 is a schematic view of an example electronic device executing instructions for displaying augmented anatomical features in accordance with the principles of the present disclosure.

In some implementations, the augmented reality device 102 recognizes and assigns the reference marker(s) 112 to one or more particular parts of the body (e.g., facial features) of the target individual 106. For example, the image capture device 108 may include an infrared camera that uses infrared laser scatter beam technology, for example, to recognize and assign the reference marker(s) 112 to the one or more particular parts of the body (e.g., facial features) of the target individual 106. In particular, the image capture device 108 may be able to create a three-dimensional reference map of the face of the target individual 106 and compare the three-dimensional reference map to reference data stored in a storage resource of the augmented device 102, such as the storage device 430 (FIG. 4). The augmented reality device 102 may use the infrared camera of the image capturing device 108 to identify the reference markers 112 on the face of the target individual 106. The augmented reality device 102 may identify the reference markers 112 on the lips, corners of the mouth, tip of the nose, or ears of the target individual 106. For example, the augmented reality device 102 may identify the reference markers 112 based on input (e.g., touch, hand gesture, etc.) from the user 104. As will be explained in more detail below, in some implementations, the augmented device 102 uses the identification information from the infrared camera, along with the identified referenced markers 112 based on the input from the user 104, to transmit data corresponding to the location of the reference markers 112 to a processing module (e.g., processor 410 of FIG. 4) to allow the augmented reality device 102 to advantageously give more individualized and specific estimates of the location of various anatomical features on the body (e.g., face) of the target individual 106, including the underlying blood vessels, nerves, and muscles.

In some implementations, the augmented reality device 102 identifies and assigns the reference marker(s) 112 by using machine learning or artificial intelligence algorithms to identify particular parts of the body of the target individual 106. The augmented reality device 102 may assign the locations of the reference markers 112 on the target individual 106 based on the locations of similar reference markers 112 on one or more other target individuals 106. The augmented reality device 102 may use machine learning or artificial intelligence algorithms to identify the target individual 106 as being a human body by detecting a silhouette of the target individual 106, recognizing body parts of the detected silhouette (e.g., limbs, crotch, armpits, or neck), and then determining the location of, and assigning, reference markers 112 based on the recognized body parts.

In the example shown, a first reference marker 112a corresponds to a navel of the target individual 106. A second reference marker 112b corresponds to a portion of a right shoulder of the target individual 106. A third reference marker 112c corresponds to a portion of a left shoulder of the target individual 106. A fourth reference marker 112d corresponds to a portion of a collarbone of the target individual 106. A fifth reference marker 112e corresponds to a portion of a left hip of the target individual 106. A sixth reference marker 112f corresponds to a portion of a right hip of the target individual 106. A seventh reference marker 112g corresponds to a portion of a sternum of the target individual 106. Reference markers 112a-112g do not represent an exhaustive list of all reference markers, but rather an exemplary list of reference markers that may be identified by augmented reality device 102. Furthermore, augmented reality device 102 may identify other reference markers in addition to reference markers 112a-112g, such as reference markers corresponding to a neck, a nose, eyes, a mouth, knees, ankles, a gluteal fold, shoulder blades, wrists, or elbows, without departing from the teachings herein. Augmented reality device 102 may also omit one or more reference markers 112a-112g, without departing from the teachings herein.

The augmented reality device 102 may determine an anatomical profile of the target individual 106. The anatomical profile may include a plurality of characteristics corresponding to the individual 106. In some implementations, the anatomical profile includes or is based on a plurality of target data, such as age or sex of the target individual 106. In some implementations, the augmented reality device 102 determines the anatomical profile based on an input (e.g., touch, hand gesture, etc.) from the user 104. In other implementations, the augmented reality device 102 uses machine learning or artificial intelligence algorithms to determine the anatomical profile. For example, the augmented reality device 102 may determine the anatomical profile based on a plurality of target data (e.g., the plurality of reference markers 112) received by the augmented reality device 102.

Figure 1C:
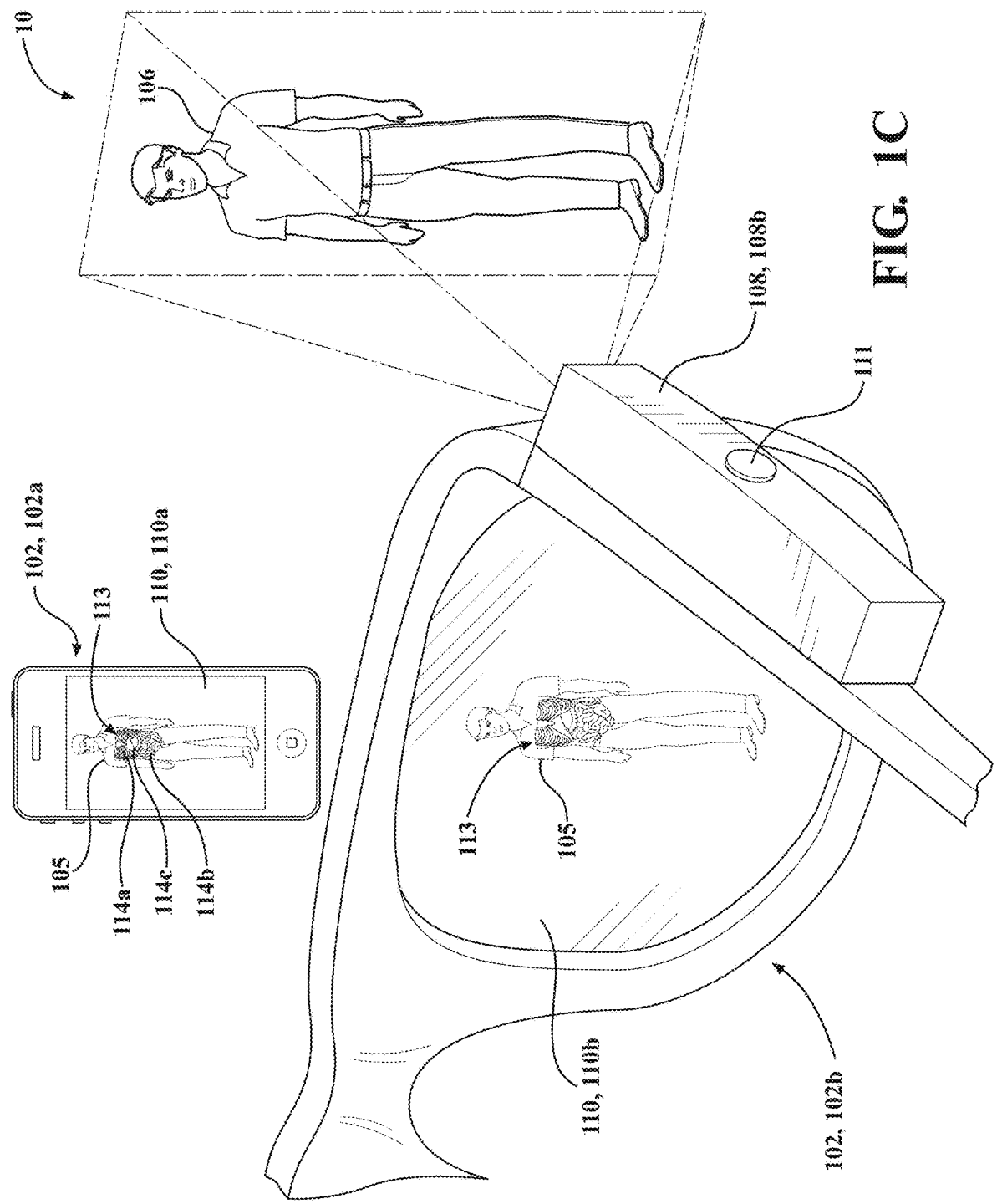
FIG. 1C illustrates an exemplary use of the augmented reality system of FIG. 1A in accordance with the principles of the present disclosure.

Referring now to FIG. 1C, exemplary augmented reality devices are shown. The augmented reality devices 102a, 102b may display a graphical representation 113 of the target individual 106. In some implementations, the augmented reality device 102 may display the graphical representation 113 even when the target individual 106 is fully clothed. This is advantageous as it saves time because the target individual 106 does not have to remove their clothing. The graphical representations 113 of the target individual may include one or more virtual images 114a-114c of anatomical features. For example, the virtual images 114a-114c may be virtual images of internal (e.g., bones or other organs) or external (e.g., skin or contours thereof) anatomical features. In some implementations, the augmented reality device 102 uses three-dimensional data corresponding to the target individual 106 to generate the graphical representations 113. In some implementations, the graphical representations 113 include virtual images 114 of a detailed underlying anatomy of the face of the target individual 106.

A method of displaying the graphical representation 113 may include various steps. For example, the method of displaying the graphical representation 113 may include identifying one or more reference markers 112 (FIG. 1B)

with the augmented reality device 102 (e.g., 102a, 102b). The augmented reality device 102 may also determine the distance from each reference marker 112 to each of the other reference markers 112 and transmit data corresponding to the distances to a processor (e.g., processor 410 of FIG. 4). The augmented reality device 102 may further perform a look up in a database (e.g., database 218 in FIG. 2) with data corresponding to reference markers 112 (e.g., memory 420 of FIG. 4). The augmented reality device 102 may use the data corresponding to reference markers 112, and in some implementations the plurality of target data, to determine data corresponding to the anatomical features' characteristics (e.g., size, location, etc.). For example, the augmented reality device 102 may use the reference markers 112 and the three-dimensional visual representation 105 of the target individual 106 created from infrared laser scatter beam technology of the image capture device 108 to create the graphical representation 113, including the virtual images 114a-c of the anatomical features. In particular, the augmented reality device 102 may transmit the data corresponding to the anatomical features' characteristics to the processor (e.g., processor 410 of FIG. 4) and display the graphical representation 113, including the virtual images 114a-c of the anatomical features, on the display 110 at a location corresponding to the target individual 106 (see FIG. 1C).

As illustrated in FIG. 1C, the second augmented reality device 102b may display the graphical representation 113 on the eyepiece display 110b, and the first augmented reality device 102a may display the graphical representation 113 on screen 110a. As previously described, the graphical representation 113 displayed on screen 110 and overlaid on top of visual representation 105 of the target individual 106 may include computer-generated virtual images (e.g., the virtual images 114a-c of the anatomical features). In the example shown, augmented reality device 102 displays, on display 110, the graphical representation 113 includes virtual images 114a-114c each representing an organ, bone, or structure in the human body.

A first virtual image 114a represents a ribcage of the human body. Virtual image 114a is overlaid on the visual representation 105 of the target individual 106 at a location approximating where the ribcage of the target individual 106 is located. A second virtual image 114b represents intestines of the human body. Virtual image 114b is overlaid on the visual representation 105 of the target individual 106 at a location approximating where the intestines of the target individual 106 are located. A third virtual image 114c represents a pancreas of the human body. Virtual image 114c is overlaid on the visual representation 105 of the target individual 106 at a location approximating where the pancreas of the target individual 106 is located. Virtual images 114a-114c do not represent an exhaustive list of all virtual image, but rather an exemplary list of virtual images that may be displayed by the augmented reality device 102 in the graphical representation 113. Furthermore, the augmented reality device 102 may display other virtual images in addition to the virtual images 114a-114c, or may omit one or more virtual images 114a-114c, without departing from the teachings herein.

The graphical representation 113, in combination with the visual representation 105, enhances the view and experience of the user 104 by creating a composite view of both real and virtual images on the display 110. The user 104 may view, through the display 110, the visual representation 105 of the target individual 106 with the virtual images 114a-114c of organs and other anatomical features represented by the graphical representation 113 of the target individual 106. The anatomical features may include organs, bones, muscles, blood vessels, tendons, ligaments, or nerves. In some implementations, the virtual images 114a-114c are not actual images of the internal organs, bones, or other bodily structures of target individual 106, but rather are representative depictions (e.g., illustrations) of those bodily structures. Allowing the augmented reality device 102 to store representative virtual images 114a-114c that can be used for any target individual 106 is advantageous because it requires less space (e.g., memory 420) for storing the virtual images 114a-114c, allowing the augmented reality device 102 to operate and display the virtual images 114a-114c at a faster speed.

In some implementations, the augmented reality device 102 may use the image capture device 108 to take a still picture or record a video of the target individual 106. The augmented reality device 102 may then overlay virtual images 114 of anatomical features onto the still picture or recorded video of target individual 106. The augmented reality device may then display the still picture or recorded video with the overlaid virtual images 114 onto the display 110. This may be advantageous, particularly for educational purposes, as it assists a healthcare professional in educating a patient about their own anatomy by showing the patient how their own individual anatomy approximately works. In other implementations, the augmented reality device 102 may be able to take a picture or record a video of the target individual 106 with the visual representation 105 that includes the virtual images 114 of organs and other anatomical features. The augmented reality device 102 may store the picture or recorded video in a storage resource, such as the storage device 430 (FIG. 4).

Figure 1D:
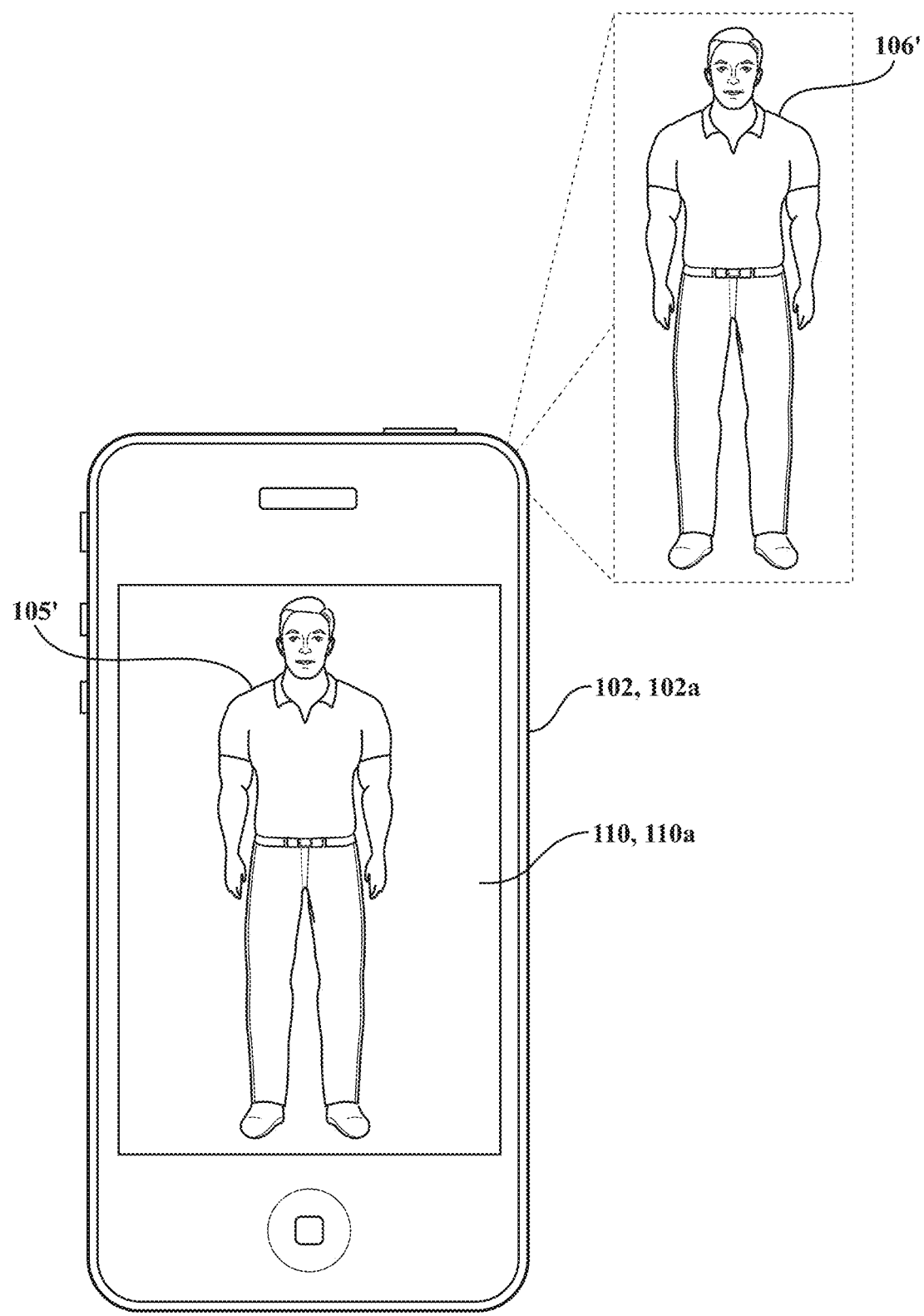
FIG. 1D illustrates an exemplary use of the augmented reality system of FIG. 1A in accordance with the principles of the present disclosure.
Figure 1E:
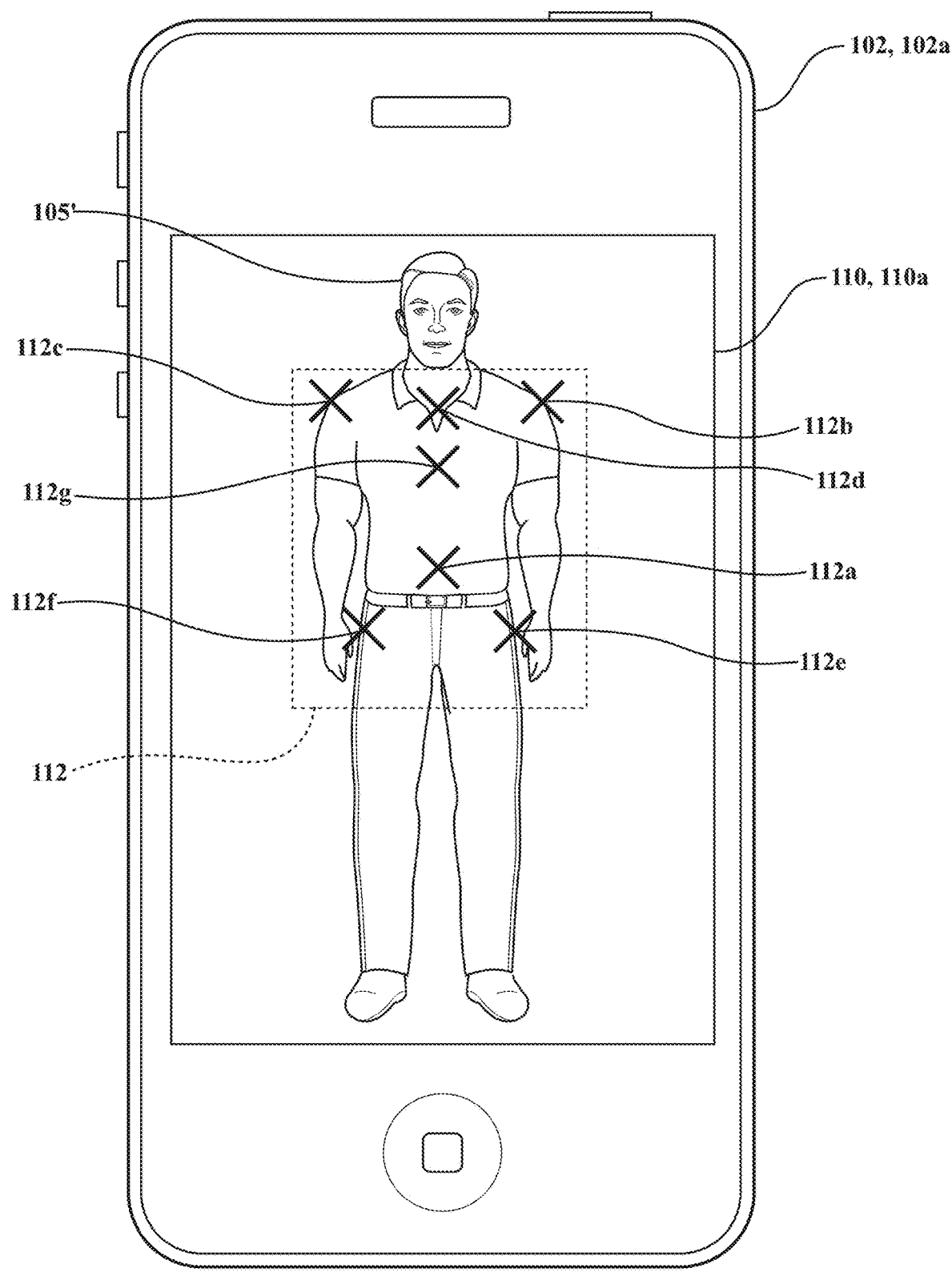
FIG. 1E illustrates an exemplary use of the augmented reality system of FIG. 1A in accordance with the principles of the present disclosure.
Figure 1F:
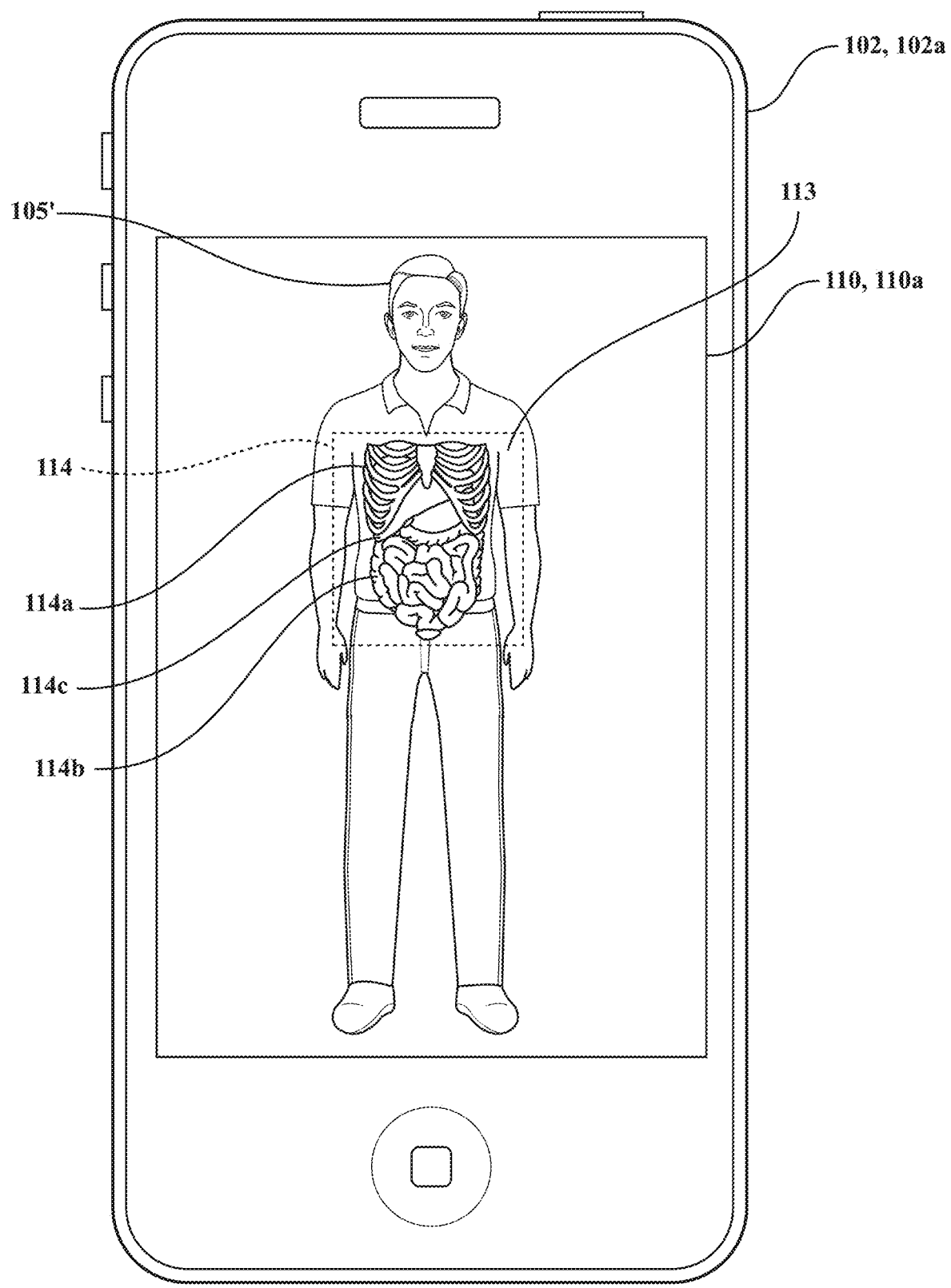
FIG. 1F illustrates an exemplary use of the augmented reality system of FIG. 1A in accordance with the principles of the present disclosure.

With reference now to FIGS. 1D-1F, in some implementations, the augmented reality device 102 (e.g., 102a, 102b) may display the anatomical profile of a target (e.g., target individual 106) based on certain anticipated changes to the target individual 106. FIG. 1D shows a visual representation 105' of an alternative target individual 106' displayed on display 110. The augmented reality device 102 may determine the visual representation 105' of the alternative target individual 106' with the image capture device 108. As illustrated in FIG. 1E, similar to the visual representation 105 of FIG. 1B, the augmented reality device 102 may identify a plurality of reference markers 112 on the visual representation 105'. In some implementations, the augmented reality device 102 may determine an anatomical profile of the alternative target individual 106'. The anatomical profile may include a plurality of characteristics corresponding to the alternative target individual 106'. As described above in reference to FIG. 1B, the anatomical profile may be based on a plurality of target data, input from the user 104, or machine learning or artificial intelligence algorithms. In some implementations, the anatomical profile may also be based on certain changes that the alternative target individual 106' may undergo. For example, the anatomical profile may be based on future weight loss or weight gain that the alternative target individual 106' will, or desires to, undergo.

FIGS. 1E and 1F show the augmented reality device 102 displaying the visual representation 105' of the alternative target individual 106' on display 110. The augmented reality device 102 displays the graphical representation 113 of the alternative target individual 106', the graphical representation 113 including virtual images 114 of anatomical features. In the example shown at FIG. 1F, the augmented reality device 102 displays the visual representation 105' of the alternative target individual 106' if the alternative target individual 106' had lost weight (FIG. 1F). The augmented reality device also overlays the graphical representation 113 that includes the virtual images 114 of anatomical features. The virtual images 114 of anatomical features may be based on the anatomical features of the alternative target individual 106' if the alternative target individual 106' lost weight. Furthermore, the visual representation 105' (FIG. 1F) of the alternative target individual 106' may be based on if the alternative target individual 106' lost weight.

Though FIG. 1F depicts the augmented reality device 102 displaying the virtual images 114 of anatomical features based on if the alternative target individual 106' lost weight, it should be noted that the augmented reality device may display virtual images 114 based on other certain changes, such as gaining weight, becoming pregnant, undergoing reconstructive or cosmetic surgery, or other changes that an individual's body may undergo. Furthermore, the augmented reality device 102 may display other virtual images 114 that show how musculoskeletal features would function under the certain changes.

With reference again to FIGS. 1E and 1F, another aspect of the augmented reality device 102 is provided. The augmented reality device 102 is configured to detect a target individual 106 by using an image capture device 108 and display a visual representation 105 of the body of the target individual 106. The augmented reality device 102 is configured to identify one or more reference markers 112 as described above with reference to FIG. 1B. The reference markers 112 are processed to identify an anatomical profile which includes a plurality of inner anatomical features 114. The augmented reality device 102 is further configured to access a database 218. The database 218 may be stored in the augmented reality device 102 or may be stored in a remote server, such as a server located in or accessible through a network 400.

Figure 1G:
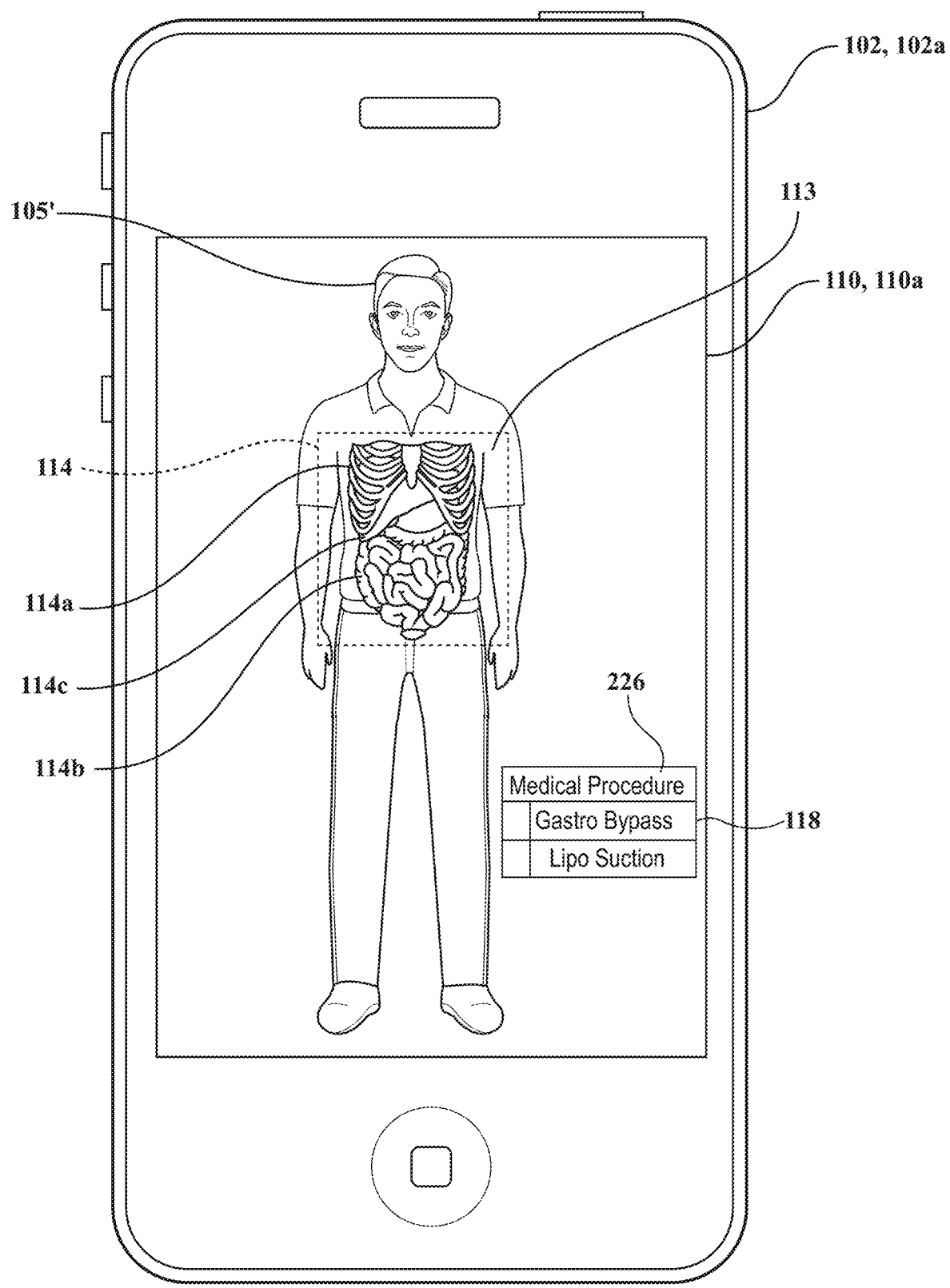
FIG. 1G illustrates an exemplary use of the augmented reality system of FIG. 1A in accordance with the principles of the present disclosure.

The augmented reality device 102 is configured to display on the display 110, a graphical representation of the inner anatomical features onto the visual representation of the body, as shown in FIG. 1G. Accordingly, a user such as a healthcare professional, is able to identify the location of the inner anatomical features without performing conventional procedures such as an x-ray, an MRI or other medical scanning operations. Such a display is helpful in assisting the healthcare professional with identifying, within a reasonable degree of accuracy, a medical condition, a location for an incision, an organ, specific portion of a muscle or tendon, or any other interior anatomic structure not externally visible. As an example, augmented reality device 102 captures an image of the patient body 106 and displays a visual representation 105 of the body. The augmented reality device 102 identifies reference markers 112a-112g and searches the database 218 to find an anatomical profile 216 corresponding to the spatial orientation and relationship of the identified reference markers 112a-112g. The graphical representation of the inner anatomical features are overlaid onto the visual representation 105 of the body.

The patient may be experiencing abdominal pain and may point to the location of the pain on the body. The healthcare professional may then be able to better identify the issue by referencing where the pain is with respect to the location of the inner anatomical features (which is displayed in the graphical representation 105), such as distinguishing between a pain located at the duodenum as opposed to the pancreas, the pancreatic duct or the like. Accordingly, the augmented reality device 102 assists the surgeon with treatment, diagnosis, patient education and the like without having to subject the patient to an x-ray, MRI or other internally invasive scanning procedures.

With reference now to FIG. 1G, another aspect of the augmented reality device 102 is provided. The database 218 includes a plurality of future state anatomical profiles 216' corresponding to a selected medical procedure 226. It should be appreciated that the database 218 may include thousands of future state anatomical profiles 216'. The augmented reality device 102 is further configured to receive the selected medical procedure 226. For instance, the augmented reality device 102 may display a menu 118 offering a selection of a plurality of medical procedures 216 such as a procedure effecting an organ, bone or muscle. Such medical procedures include a liposuction, a gastrointestinal bypass, a nose job or the like.

In operation, the augmented reality device 102 processes the reference markers 112 to determine which anatomical profile 216 stored in the database 218 matches the reference markers 112 identified. The user then selects a medical procedure 226 and retrieves the future state anatomical profile 216' which corresponds to the selected medical procedure 225. The augmented reality device 102 then modifies the inner anatomical features 114 based on the selected medical procedure 226. As an example, FIG. 1B depicts the augmented reality device 102 identifying a plurality of reference markers 112 on the target individual 106.

With reference now to FIG. 1G the augmented reality device 102 searches the database 218 to find an anatomical profile corresponding to the reference markers 112. For example, the augmented reality device 102 may use the distance between reference markers 112 to find an anatomical profile having similar distances between the reference markers. For example, if the patient is a male, that is 5'10" having the left and right shoulders 112c and 112b that are spaced apart from each other 18 inches, the left and right hips 112f and 112e that are spaced apart from each other 19 inches, the augmented reality device 102 searches the database 218 to find an anatomical profile of a male that is 5'10 having reference markers 112 of similar spacing. It should be appreciated that the more reference markers may be used to determine the corresponding anatomical profile other than just the left and right shoulders 112c and 112b and the left and right hips 112f and 112e. The inner anatomical features are then displayed on the graphical representation as shown in FIG. 1G.

In another aspect, the augmented reality device 102 may be further configured to scale the inner anatomical features of the selected anatomical profile based upon the size of the target individual 105 relative to the selected anatomical profile. The augmented reality device 102 may make a determination that the target individual is larger or smaller than the selected anatomical profile. The augmented reality device 102 may be further configured to increase or decrease the size of the inner anatomical features associated with the selected anatomical profile so as to fit the image and the reference markers 112. As an example, for a target individual 105 that is larger than the selected anatomical profile, the inner anatomical features of the selected anatomical profile is magnified. Such an aspect may be beneficial in instances where the database 218 is populated with a discrete number of anatomical profiles. Thus, the augmented reality device 102 is configured to display the inner anatomical features onto a visual representation 105 of the target individual 106 using less processing resources relative to an aspect where the database 218 is populated with hundreds of anatomical profiles.

As an example, the database 218 may be populated with only eight (8) anatomical profiles for a respective male and female version of an infant, child, adult and elderly for a total of sixty-four (64) anatomical profiles. In such an aspect, the augmented reality device 102 processes the sixty-four (64) anatomical profiles to select an anatomical profile which matches the spatial dimensions of the reference markers 112 the closest. For instance, the target individual 106 may be a male adult that is 5'11". The database 218 may be populated with a male adult that is 5'8 and another that is 6'2". The augmented reality device 102 selects the anatomical profile of the adult male that is 6'2" in cases where the anatomical profile of the adult male that is 6'2" matches the reference markers 112 more closely than the anatomical profile of the adult male that is 5'8". The augmented reality device 102 scales the inner anatomical features of the selected anatomical profile so as to fit within the visual representation 105 of the body of the target individual 106. Using the same example, the augmented reality device 102 may shrink the inner anatomical features of the selected anatomical profile so as to fit within the smaller visual representation of the target individual 106.

It should be appreciated that not all of the inner anatomical features of the selected anatomical profiles need to be scaled. For instance, the augmented reality device 102 may be further configured to determine which of part of the body of the target individual is larger or smaller than the selected anatomical profile, wherein the inner anatomical features of the body part that is larger or smaller than the selected anatomical profile is scaled. As an example, the augmented reality device 102 may magnify the lungs of the selected anatomical profile in instances where a target individual 106 has a chest cavity that is larger than the selected anatomical profile. The magnification is made so as to overlay the lung in proportion to visual representation 105 of the target individual 106.

In yet another aspect, the augmented reality device 102 may be further configured to process a body type along with the reference markers 112. For example, it may be assumed that the target individual 106 shown in FIGS. 1A and 1B may be considered a normal body type, the target individual 106 shown in FIGS. 1D and 1E may be considered an athletic body type, and the target individual 106 shown in FIGS. 1I and 1K may be considered an overweight body type. The augmented reality device 102 processes the body type with a silhouette of the target individual 106 and the selected anatomical profile so as to provide an overlay of other anatomical features such as fatty layer, muscular thickness and the like. The augmented reality device 102 may be further configured to process the silhouette of the target individual and the selected anatomical profile so as to overlay other features of the inner anatomy of the individual target 106 such as the blood vessels, nerves and organs corresponding to the selected anatomical profile. It should be appreciated that such a feature provides additional detail to assist the healthcare professional in providing care, education, perform a diagnosis and the like.

For illustrative purposes, an operation of the augmented reality device processing a body type and a silhouette along with the selected anatomical profile is provided. The augmented reality device 102 detects the target individual 106 by using an image capture device 108 and processes the visual representation 105 of the target individual so as to determine a silhouette. The silhouette may be determined by implementing any known or later developed image processing technique for edge detection currently known or later developed.

In one aspect, the augmented reality device 102 may process the silhouette to determine a body type. The body type may be determined by processing the spatial relationship between the reference markers, or opposing edges of the silhouette. As an example, by determining that a distance between opposing edges around the waist exceed a distance between opposing edges of each shoulder in an image taken from the same perspective, the reality device 102 may determine that the target individual has an overweight body type. As another example, the reality device may determine that the target individual 106 has an athletic body type by determining that a distance between opposing edges of the waist is smaller than a distance between opposing edges of each shoulder in an image taken from the same perspective. Alternatively, the body type may be simply inputted by using a drop down menu, a keyboard or any other input currently known or later developed.

In cases, where the augmented reality device 102 determines, by image processing or by an input, that the body type is overweight, the augmented reality device 102 may scale inner anatomical features to be commensurate with the body type. For instance, a fatty layer may be made thicker, relative to a fatty layer of a normal body type, wherein the inner anatomical features of the selected anatomical profiles are scaled to fit behind the thickened fatty layer. The thickening of the fatty layer may be made commensurate with the silhouette, and may be further refined by processing the reference markers 112. In instances where the body type is athletic, the fatty layer may be made thinner relative to a fatty layer of a normal body type, and the muscles enlarged relative to a normal body type. It should be appreciated that the examples provided herein are illustrative and not limiting and that other inner anatomical features may be adjusted based upon the determined body type.

It should be appreciated that though the description of operation of the augmented reality device 102 according to the aspect above is provided in a global manner, the reality device 102 may be operated in a granular manner that is specific to a particular body part. For instance, the adjustment of a fatty layer may be made only to a portion of the body which is deemed to fall outside the specifications of a normal body type. For instance, the augmented reality device 102 may determine, based upon the silhouette, that only the waist is overweight and the remaining body is normal. In such an aspect, the augmented reality device 102 is configured to only thicken the fatty layer around the waist and display the fatty layer of the remaining body part as being normal. It should be further appreciated that the adjustment of the anatomical features based upon the body type may be done automatically, or based upon an input from the healthcare professional. That is, the augmented reality device 102 may operate without processing a silhouette. Thus, the graphical presentation of the inner anatomical features are overlaid onto the visual representation of the body without any adjustments made to inner anatomical features such as the fatty layer, muscles, or the like. The healthcare professional, may then select an option or otherwise input a desire to modify the graphical representation with the silhouette of the determined body type.

Figure 1H:
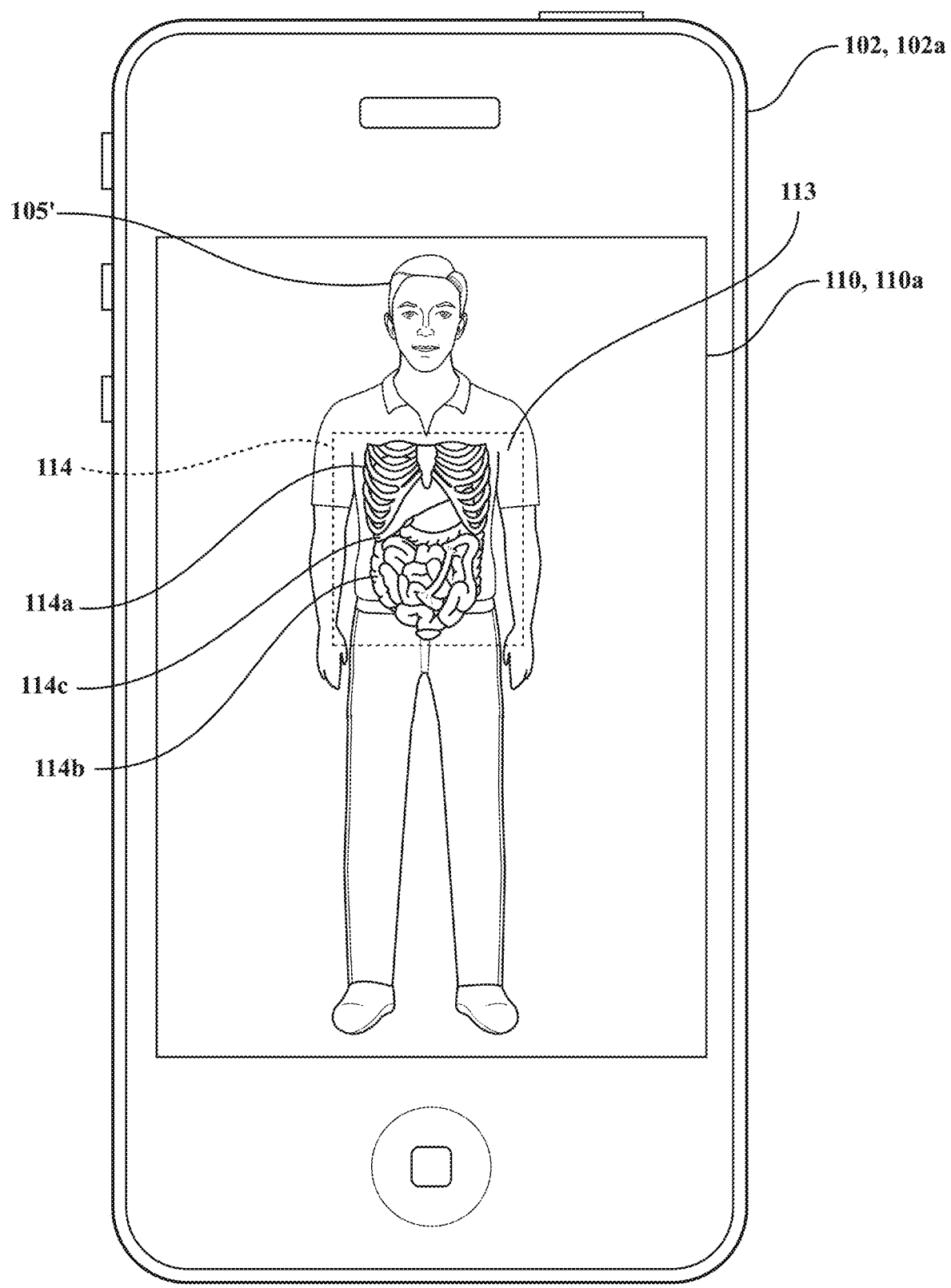
FIG. 1H illustrates an exemplary use of the augmented reality system of FIG. 1A in accordance with the principles of the present disclosure.

With reference now to FIG. 1H, the graphical representation 113 is modified relative to FIG. 1G. In particular, the augmented reality device 102 is configured to receive a selected medical procedure 226. For illustrative purposes, the medical procedure 226 is selected by a drop down menu 118 (shown in FIG. 1G). However, other means for inputting the selected medical procedure 226 may be adapted for use herein, illustratively including a keyboard, voice input or the like. For illustrative purposes, the selected medical procedure 226 is a gastric bypass. The augmented reality device 102 selects a future state anatomical profile 216' corresponding to the selected medical procedure 226. In this case, the augmented reality device 102 modifies the inner anatomical feature 114 (namely the stomach) by overlaying the stomach shown in FIG. 1G with the future state of anatomical profile 216' determined by the augmented reality device 102, as shown in FIG. 1H. Accordingly, in this aspect, the patient is able to see the effect a surgical procedure has on the inner anatomical features of the patient. In particular, the patient may be able to see what his inner anatomical features look like before the medical procedure, as shown in FIG. 1G and after the medical procedure as shown in FIG. 1H.

In another aspect of the augmented reality device 102, the database 218 further includes a plurality of diseases, inherited conditions and/or anatomical variants. As an example, the database may store different types of diseases such as cancer, heart disease, diabetes and the like; inherited conditions such as cystic fibrosis, down syndrome and the like; anatomical variants may include anatomical variants of anatomical features such as the gallbladder, kidney, liver and the like. The augmented reality device 102 is further configured to determine an anatomical profile corresponding to the identified disease, the identified inherited condition or the identified anatomical variant and generate a graphical representation which a visual representation of the body modified with the inner anatomical features based on the determined anatomical profile. As such, the augmented reality device 102 may be helpful in showing the patient and/or surgeon the effects of a disease or inherited condition on the inner anatomical features.

In another aspect, the database 218 includes anatomical profiles having at least one of the diseases, inherited conditions and/or anatomical variants. In such an aspect, the augmented reality device 218 simply selects the anatomical profile corresponding the identified reference markers 112a-112g having an identified disease, inherited conditions and/or anatomical variants as the case may be and displays the inner anatomical features associated with the selected anatomical profile. In such an embodiment, it is preferable for the patient to identify the disease, inherited condition or anatomical variant, as the case may be. This may be done by an input field and entered using conventional input means such as a keyboard, voice input, a mouse or the like.

As an example, the surgeon or nurse inputs a disease into the augmented reality device 218. The augmented reality device 218 detects the target individual and displays a visual representation of the body. The augmented reality device 218 processes the reference markers 112a-112g to identify an anatomical profile having reference markers with the same spatial dimensions and the disease entered into the augmented reality device 218. The inner anatomical features of the selected anatomical profile is mapped onto the visual representation of the body.

Figure 1I:
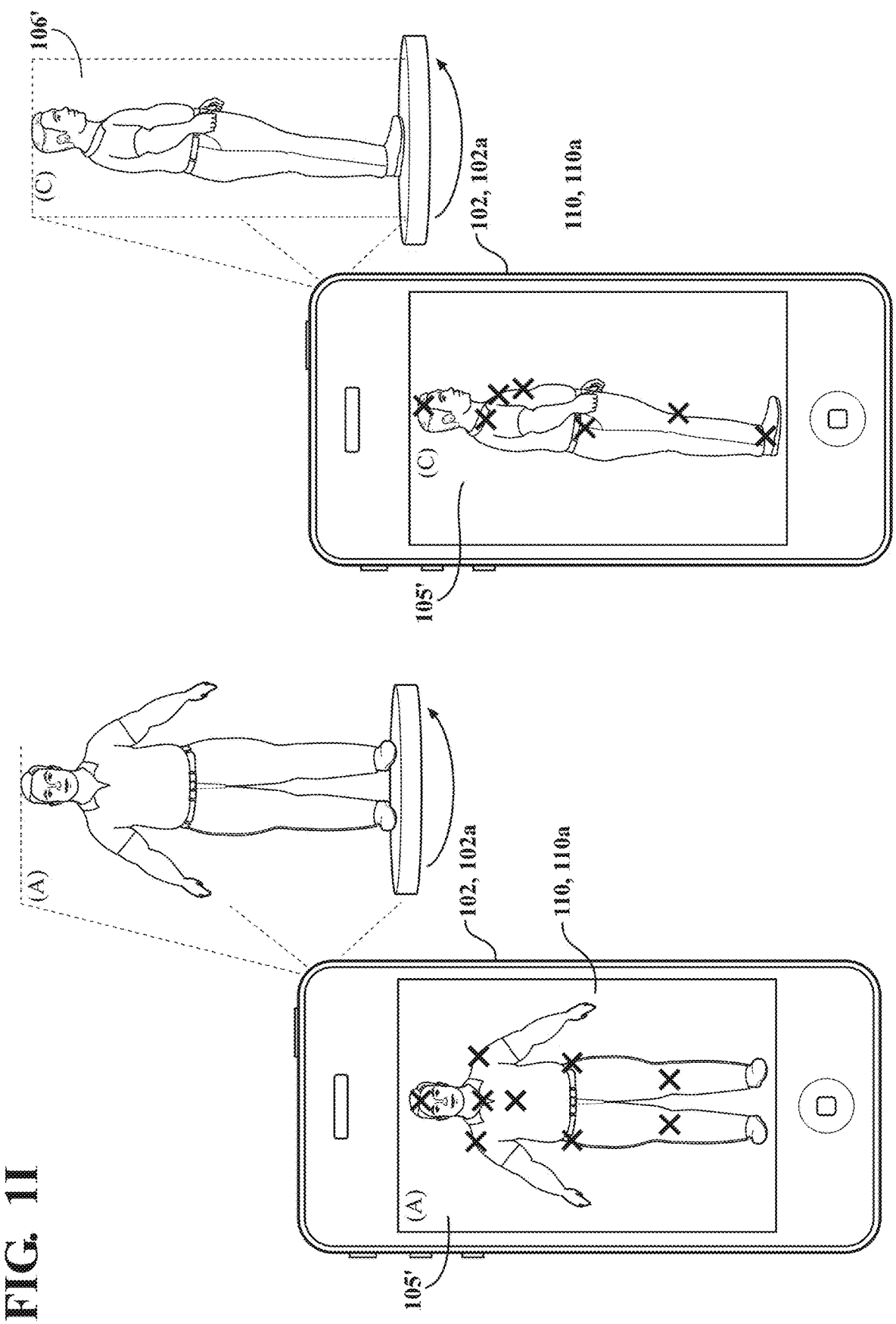
FIG. 1I illustrates an exemplary use of the augmented reality system of FIG. 1A in accordance with the principles of the present disclosure.

With reference now to FIG. 1I, another aspect of the augmented reality device 102 is provided. FIG. 1I depicts the augmented reality device 102 mapping a target individual 106. The augmented reality device 102 includes an image capture device 108 configured to generate an initial three-dimensional representation 113' of the body. For instance, the image capture device 108 may be a LIDAR camera or an infrared laser scatter beam device. FIG. 1I depicts the initial three-dimensional representation 113' as still images take from the front of the target individual 106 and the side of the target individual. However, it should be appreciated that the initial three-dimensional representation 113' depicts the entirety of the target individual 106, and thus may be generated by taking a number of still images or a video. In one aspect, the target individual 106 may stand on a platform 120 which may rotate 360 degrees as indicated by the arrow. The augmented reality device 102 is placed a predetermined distance from the target individual 106 and the image capture device 108 is actuated so as to map the target individual. FIG. 1I depicts the images taken as the target individual 106 is rotated. It should be appreciated that the initial three-dimensional representation 113' of the target individual 106 may be generated in another manner, for instance the target individual 106 may stand still as the augmented reality device 102 rotates about the 106. Alternatively, multiple augmented reality devices 102 may be positioned at different locations around the target individual 106 and the images captured from each of the augmented reality devices 102 are compiled together and processed to generate the initial three-dimensional representation 113'.

The augmented reality device 102 identifies one or more reference markers 112 as described above with reference to FIG. 1B. It should be appreciated that the reference markers 112 may be identified in real time or after the three-dimensional representation of the body has been generated. The augmented reality device 102 is further configured to determine a preferred anatomical profile 216" based upon the plurality of reference markers 112. The preferred anatomical profile 216" being a profile representative of a fit and healthy human which may be based upon anatomical features which may be extrapolated from the reference markers 112. The anatomical features include not only the reference markers 112 but also aspects such as the height and body shape of the target individual 106.

Figure 1J:
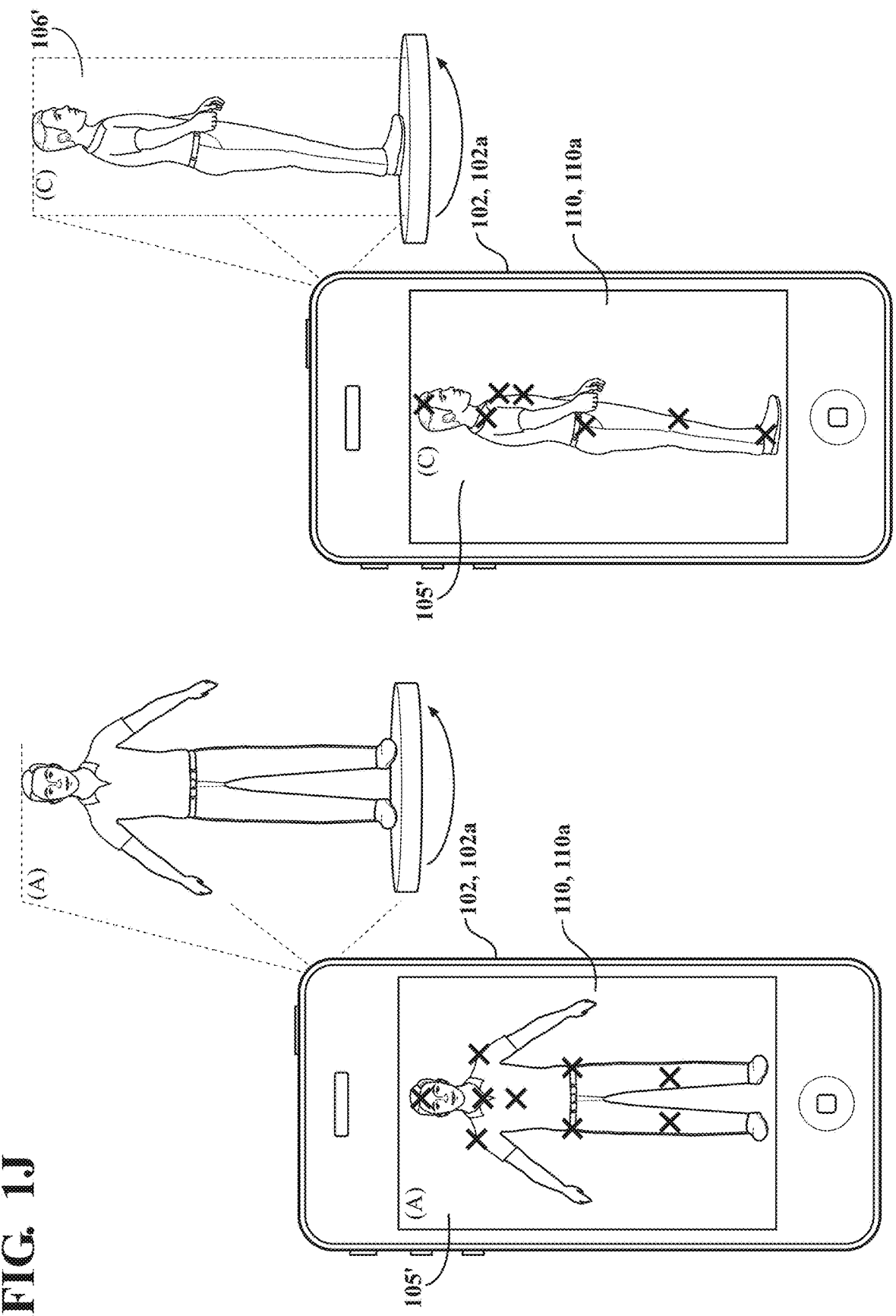
FIG. 1J illustrates an exemplary use of the augmented reality system of FIG. 1A in accordance with the principles of the present disclosure.

With reference now to FIG. 1J, the augmented reality device 102 is further configured to modify in three dimensions, the initial three-dimensional representation 113' of the body with the preferred anatomical profile 216" so as to generate a modified initial three-dimensional representation 228. The modified initial three-dimensional representation 228 is the initial three-dimensional representation of the body 113' which is shaped to conform to the shape of the preferred anatomical profile 216". The augmented reality device 102 displays a graphical representation of the modified initial three-dimensional representation 228 of the body.

The augmented reality device 102 may be further configured to receive a selected medical procedure 226 relating to a desired body part, wherein the desired body part of the initial three-dimensional representation 113' of the body is replaced with a corresponding body part taken from the preferred anatomical profile 216". The augmented reality device 102 displays the initial three-dimensional representation 113' of the body with the corresponding desired body part taken from the preferred anatomical profile 216".

In operation, the augmented reality device 102 processes the reference markers 112 to determine which preferred anatomical profile 216" stored in the database 218 matches the initial three-dimensional representation 113' of the body. The augmented reality device 102 then processes the initial three-dimensional representation 113' of the body so as to adjust the contours of the initial three-dimensional representation 113' of the body to match the contours of the preferred anatomical profile 216", which is displayed. As such, the patient can see what they would actually look like if their body were adjusted to the preferred anatomical profile. The resulting image is it is not just a preferred profile overlaid onto the patient, but it is the patient's body shape modified, stretched, shrunken and the like. Accordingly, it is preferred that the patient bare as much skin as possible when the initial three-dimensional representation 113' of the body is generated, as the skin of the patient will be modified to assume the shape of the preferred anatomical profile 216".

With reference again to FIG. 1K, the augmented reality device 102 searches the database 218 to find a preferred anatomical profile 216" based on the plurality of reference markers 112. As described above, this may be done by determining the distance between the reference markers. It should be appreciated that the database may include hundreds of preferred anatomical profiles 216" which are representative of a male that is 5'10". For instance one of the preferred profiles is of a male that is 5'10" having the left and right shoulders 112c and 112b that are spaced apart from each other 18 inches, the left and right hips 112f and 112e that are spaced apart from each other 19 inches. Another of the preferred profiles of a male that is 5'10" having the left and right shoulders 112c and 112b that are spaced apart from each other 17 inches, the left and right hips 112f and 112e that are spaced apart from each other 17 inches. As stated above, the preferred anatomical profiles 216" are a three-dimensional representation of a fit and healthy person. The augmented reality device 102 processes the initial three-dimensional representation 113' of the body so as to adjust the contours of the initial three-dimensional representation 113' of the body to match the contours of the preferred anatomical profile so as to generate modified initial three-dimensional representation 228.

FIG. 1J depicts the patient shown in FIG. 1I after the initial three-dimensional representation 113' of the body is adjusted to the contours of the preferred anatomical profile 216". The modified initial three-dimensional representation 228 of the body may be displayed on the augmented reality device 102 and may be casted to another display which is preferably larger so that the patient can view modified initial three-dimensional representation 228. The modified initial three-dimensional representation 228 may be rotated so that the patient can fully appreciate the change in his or her body. Further, as it is the initial three-dimensional representation 113' of the body that is adjusted, the user can appreciate the change in his or her own skin. That is, the initial three-dimensional image 113' is adjusted, not replaced by the preferred anatomical profile 216".

Figure 1K:
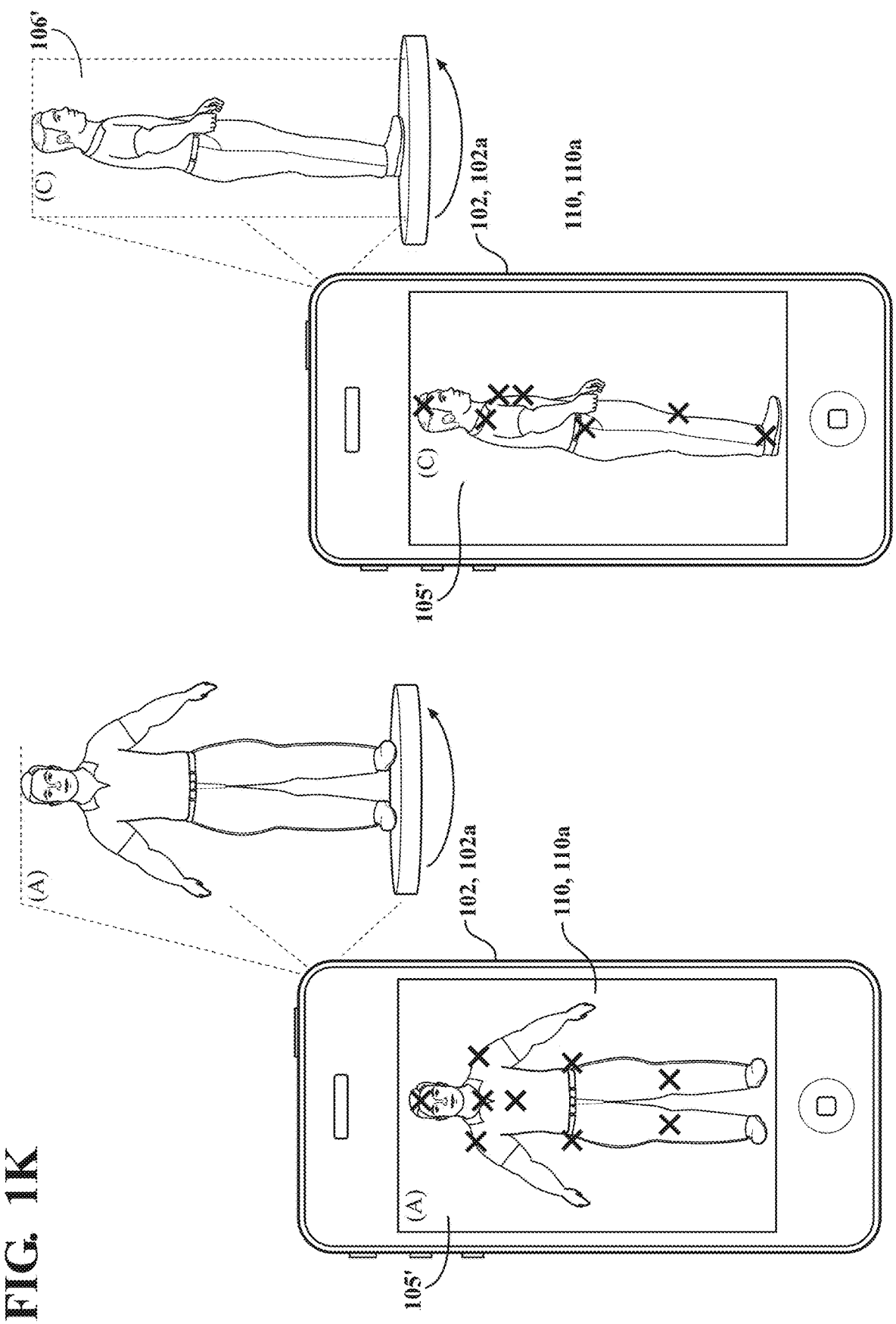
FIG. 1K illustrates an exemplary use of the augmented reality system of FIG. 1A in accordance with the principles of the present disclosure.

FIG. 1K depicts an embodiment where only a selected body part is adjusted. In one aspect, the augmented reality device 102 may be configured to process a selected medical procedure 226. As described above, the selected medical procedure 226 may be input by a drop down menu 118 or a keyboard, voice input or the like. For illustrative purposes, the selected medical procedure 226 is shown as a liposuction of the belly fat. Thus, the display 110 depicts the initial three-dimensional representation 113' modified with the belly of the preferred anatomical profile 216". In another aspect, the user may simply select a body part to be replaced by the corresponding body part of the preferred anatomical profile 216" of the body. The user may select the body part by touching the body part displayed on a touch screen display 110, through voice command or other known inputs such as a mouse or a stylus. Accordingly, in this aspect, the patient is able to see the what his or her actual body would look like should the body be modified to be the shape and contour of a preferred anatomical profile. In other words, the modified initial three-dimensional representation 228 a modification of a selected body part of the initial three-dimensional representation 113' with the corresponding body part of the preferred anatomical profile 216". Accordingly, FIG. 1K depicts that the arms, neck, legs, etc. of the patient remains the same as shown in FIG. 1I and it is only the belly that is modified to be commensurate with a belly of the preferred anatomical profile 216". As such, the patient will be able to see how he or she looks after a selected medical procedure is performed which assists in the patient's decision to have other procedures performed.

Figure 2:
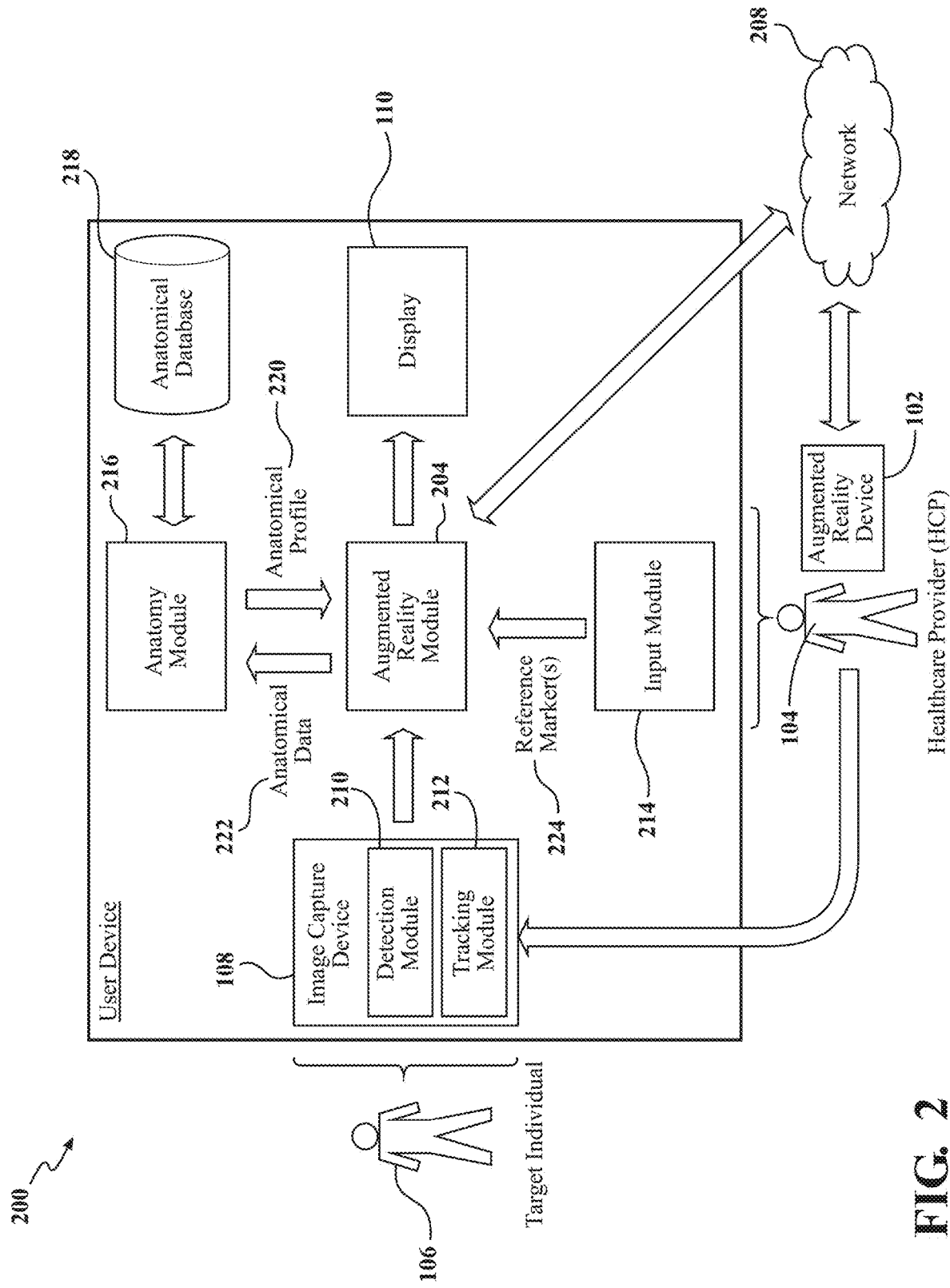
FIG. 2 is a block diagram illustrating an exemplary augmented reality system in accordance with the principles of the present disclosure.

With reference now to FIG. 2, in some implementations, an exemplary system 200 for displaying augmented anatomical features (e.g., virtual images 114a-114c) provides the user 104 (e.g., a healthcare provider) with access to an augmented reality module 204 to enhance a user's 104 view of a target individual 106. The system 200 may include a network 208 that provides access to the augmented reality module 204 that provides for the performance of services on remote devices. Accordingly, the network 208 allows for interaction between the user 104 and the augmented reality module 204. For instance, the augmented reality module 204 may provide the user 104 access to the augmented reality module 204 and receive event data inputted by the user 104 associated with the user's 104 interaction with the augmented reality module 204. In turn, augmented reality module 204 may store event data in a storage resource.

The network 208 may include any type of network that allows sending and receiving communication signals, such as a wireless telecommunication network, a cellular telephone network, a time division multiple access (TDMA) network, a code division multiple access (CDMA) network, Global system for mobile communications (GSM), a third generation (3G) network, fourth generation (4G) network, a satellite communications network, and other communication networks. The network 208 may include one or more of a Wide Area Network (WAN), a Local Area Network (LAN), and a Personal Area Network (PAN). In some examples, the network 208 includes a combination of data networks, telecommunication networks, or a combination of data and telecommunication networks. An augmented reality device 102 and augmented reality module 204 communicate with each other by sending and receiving signals (wired or wireless) via the network 208. In some examples, the network 208 provides access to cloud computing resources, which may be elastic/on-demand computing and/or storage resources available over the network 208. The term 'cloud' services generally refers to a service performed not locally on a user's device (e.g., device 102), but rather delivered from one or more remote devices accessible via one or more networks 208.

The augmented reality device 102 may include, but is not limited to, a portable electronic device (e.g., smartphone, cellular phone, personal digital assistant, personal computer, or wireless tablet device), a wearable augmented reality device, or any other electronic device capable of capturing images and overlaying computer-generated or virtual images (e.g., virtual images 114a-114c) over a real world view (e.g., the visual representation 105). The augmented reality device 102 includes data processing hardware (a computing device that executes instructions), memory hardware, and a display 110 in communication with the data processing hardware. Input module 214 provides the user 104 access to interacting with the augmented reality module 204 through the augmented reality device 102. In some examples, the input module 214 includes a keyboard, touchpad, mouse, microphones, eye-tracking device, gesture tracking device, and/or a camera for allowing the user 104 to input data. In addition to or in lieu of the display 110, augmented reality device 102 may include one or more speakers to output audio data to the user 104.

In some implementations, the user 104 may interact with the input module 214 by inputting data corresponding to reference markers 224. The reference markers 224 may correspond to locations on the target individual 106. Data corresponding to the reference markers 224 is then sent to the augmented reality module 204. The augmented reality module 204 may communicate with an anatomy module 216. For instance, the augmented reality module 204 may send anatomical data 222 corresponding to the reference markers 224 to the anatomy module 216. The augmented reality module 204 may then request data corresponding to visual representations (e.g., virtual images 114a-114c) of anatomical features from the anatomy module 216. The anatomy module 216 may then retrieve data corresponding to the visual representations of anatomical features, future state anatomical profile or preferred anatomical profile from the database 218. The anatomy module 216 may then generate an anatomical profile 220 to be displayed on the display 110.

The augmented reality device 102 may include the image capture device 108 having a detection module 210 and a tracking module 212. The detection module 210 and tracking module 212 may obtain visual data corresponding to the target individual 106 and send it to the augmented reality module 204. The visual data may be data corresponding to the current real world view of the image capture device 108 and may include data such as the distance between the target individual 106 and the augmented reality device 102, whether the target individual 106 is in motion or at rest, or any other data that corresponds to the visualization of the target individual 106 by the augmented reality device 102. The image capture device 108 may send data from the detection module 210 and the tracking module 212 to the augmented reality module 204. The augmented reality module 204 may use the data from the detection module 210 and the tracking module 212 corresponding to the image capture device's 108 real world view, coupled with virtual images of the anatomical profile 216 to create a composite enhanced view of the target individual 106 on the display 110.

Figure 3A:
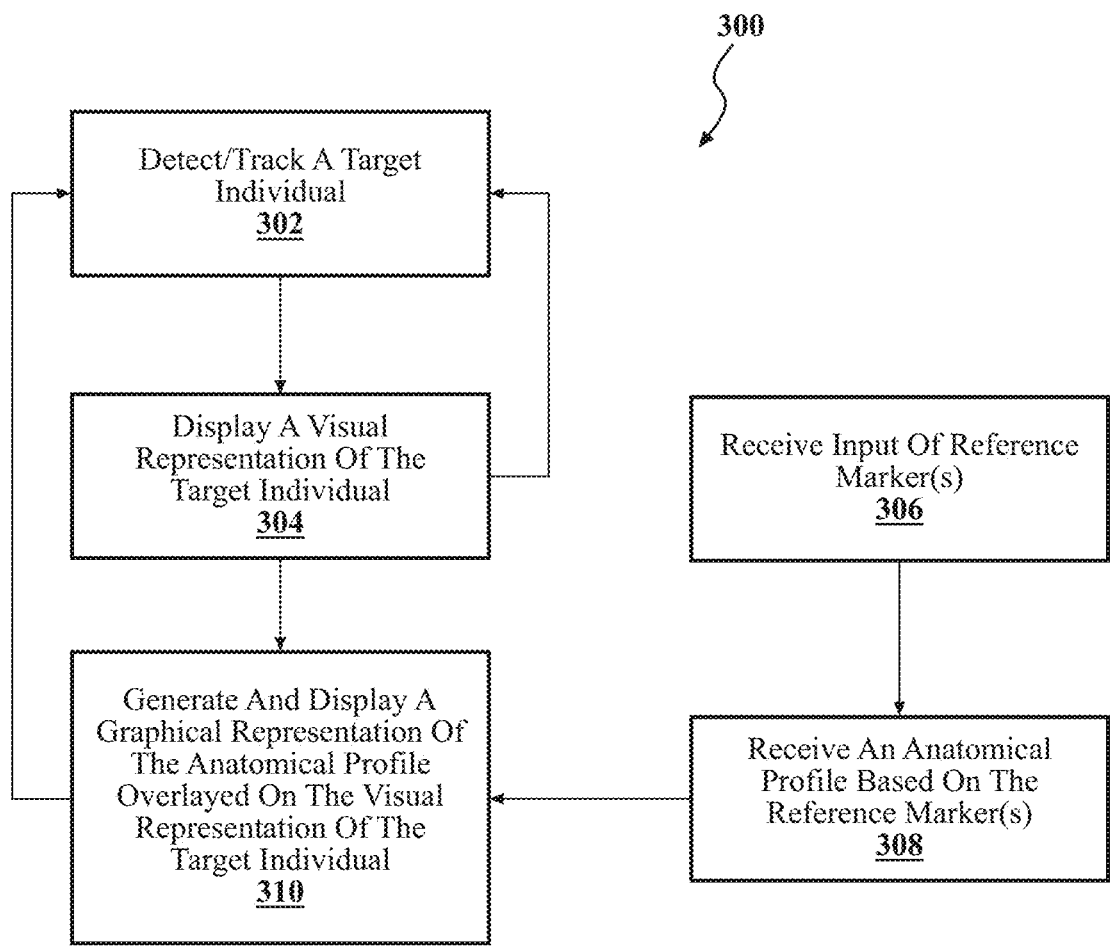
FIG. 3A is a block diagram illustrating an exemplary method for displaying augmented anatomical features in accordance with the principles of the present disclosure.

FIG. 3A is a flow chart illustrating a method 300 for displaying augmented anatomical features (e.g., virtual images 114a-114c) in accordance with an example implementation of the disclosed technology. According to one example, the method 300 may be performed by an electronic device, such as the augmented reality device 102. The method 300 begins at block 302 where the augmented reality device detects a target individual (e.g., target individual 106) and tracks the target individual. The target individual has a body. For example, at block 302, the image capture device 108a, 108b may detect and/or track the target individual 106 via the detection module 210 and/or the tracking module 212.

At block 304, the method includes displaying, on a display (e.g., display 110), a visual representation of the body. For example, at block 302, the display 110a, 110b may receive and display the visual representation 105, 105' from the augmented reality module 204. In some implementations, after block 304, the method may return to block 302. In other implementations, the method may advance to block 306.

At block 306, the method includes identifying a plurality of reference markers (e.g., reference markers 112) on the visual representation (e.g., the visual representation 105, 105') of the body. For example, the augmented reality device 102 may receive the reference markers 112 from the user's interaction with the display 110a, 110b, machine learning, or another previously-described method. In some implementations, the augmented reality device 102 may receive an input of reference markers 112 from the user 104 and receive and generate the graphical representation 113 from the augmented reality module 204.

At block 308, the method includes determining, at a processor, an anatomical profile (e.g., anatomical profile 216) of the target individual based on the plurality of reference markers. The anatomical profile may include a plurality of characteristics (e.g., age, gender, etc.) corresponding to the target individual. In some implementations, the augmented reality device 102 receives an anatomical profile based on the reference markers 112. For example, the anatomy module 216 may transmit the anatomical profile to the augmented reality device 102 through the augmented reality module 204.

At block 310, the method includes displaying, on the display, graphical representations (e.g., virtual images 114a-114c) of the anatomical features overlaid on the visual representation 105, 105' of the body. The graphical representations of the anatomical features may be oriented on the visual representation of the body based on the anatomical profile. In some implementations, the augmented reality device generates and displays a graphical representation of the anatomical profile overlaid on the visual representation of the target individual. In one aspect, the anatomical profile includes inner anatomical features, and the graphical representation of the inner anatomical features of the anatomical profile are overlaid on the visual representation of the target individual. Following block 310, the method 300 may conclude.

Figure 3B:
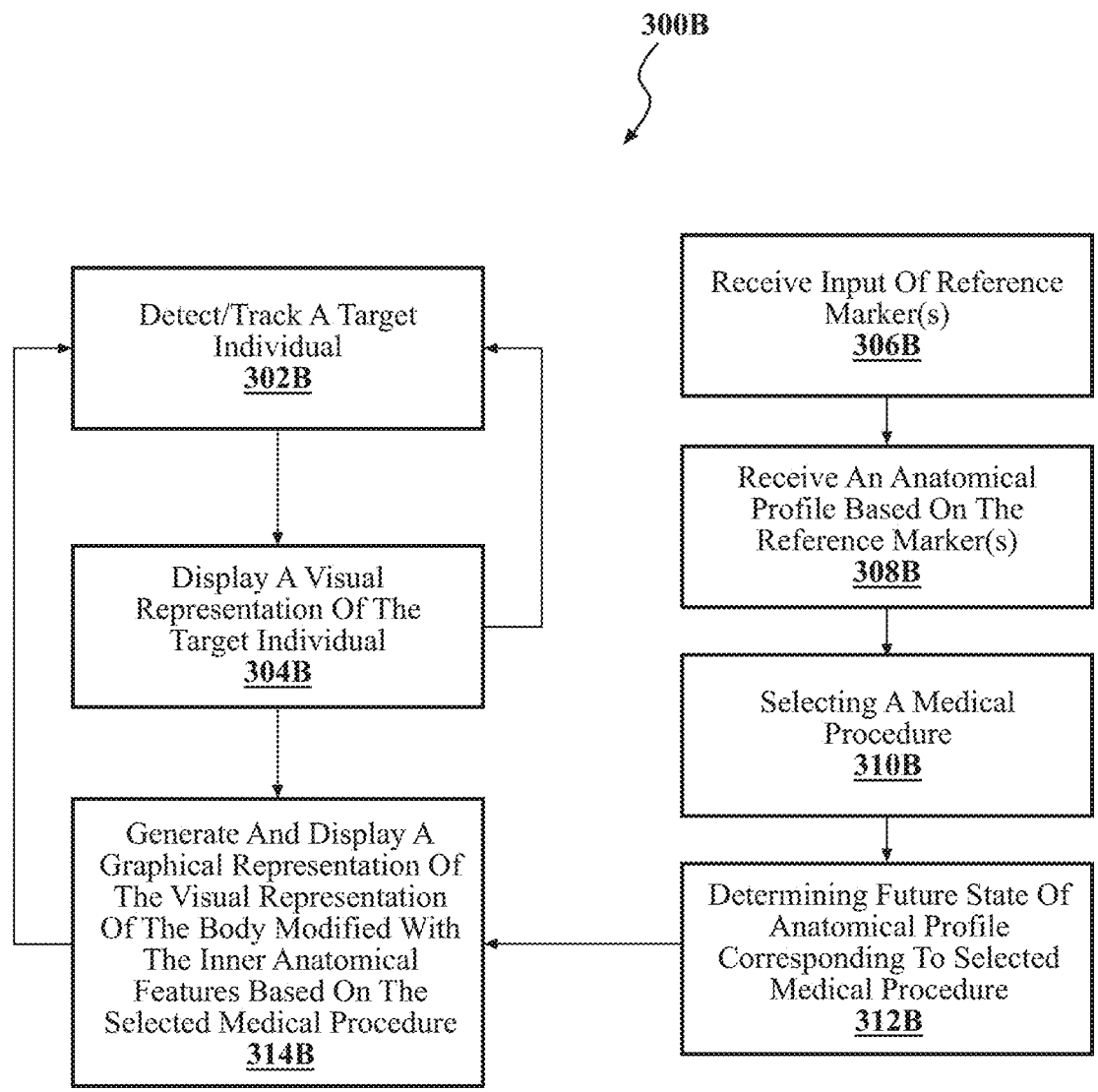
FIG. 3B is a block diagram illustrating an exemplary method for displaying a modified inner anatomical features of a patient based on a selected medical procedure.

FIG. 3B is a flow chart illustrating a method 300B for displaying a modified inner anatomical features of a patient based on a selected medical procedure. According to one example, the method 300B may be performed by an electronic device, such as the augmented reality device 102. The method 300B begins at block 302B where the augmented reality device detects a target individual (e.g., target individual 106). The target individual has a body. For example, at block 302, the image capture device 108a, 108b may detect the target individual 106 via the detection module 210 and/or the tracking module 212.

At block 304B, the method includes displaying, on a display (e.g., display 110), a visual representation of the body. For example, at block 302, the display 110a, 110b may receive and display the visual representation 105, 105' from the augmented reality module 204. In some implementations, after block 304, the method may return to block 302. In other implementations, the method may advance to block 306B.

At block 306B, the method includes identifying a plurality of reference markers (e.g., reference markers 112) on the visual representation (e.g., the visual representation 105, 105') of the body. For example, the augmented reality device 102 may receive the reference markers 112 from the user's interaction with the display 110a, 110b, machine learning, or another previously-described method. In some implementations, the augmented reality device 102 may receive an input of reference markers 112 from the user 104 and receive and generate the graphical representation 113 from the augmented reality module 204.

At block 308B, the method includes determining, at a processor, an anatomical profile (e.g., anatomical profile 216) of the target individual based on the plurality of reference markers, the anatomical profile includes a plurality of inner anatomical features. The anatomical profile may include a plurality of characteristics (e.g., age, gender, etc.) corresponding to the target individual. In some implementations, the augmented reality device 102 receives an anatomical profile based on the reference markers 112. For example, the anatomy module 216 may transmit the anatomical profile to the augmented reality device 102 through the augmented reality module 204.

At block 310B, the method includes selecting a medical procedure. The medical procedure may be selected by choosing from a drop down menu, or may be verbally inputted into an augmented reality device 102 using a keyboard, voice command or the like. The medical procedure is a procedure effecting an organ, bone or muscle. Such medical procedures include a liposuction, a gastrointestinal bypass, a nose job or the like.

At block 312B, the method includes the step of determining a future state anatomical profile corresponding to the selected medical procedure. For instance, the future state anatomical profile may be one of thousands of future state anatomical profiles stored in the database 218 which corresponds to the anatomical profile.

At block 314B, the method includes displaying, on the display, graphical representations (e.g., virtual images 114a-114c) of the visual representation of the body modified with the inner anatomical features based on the selected medical procedure.

Figure 3C:
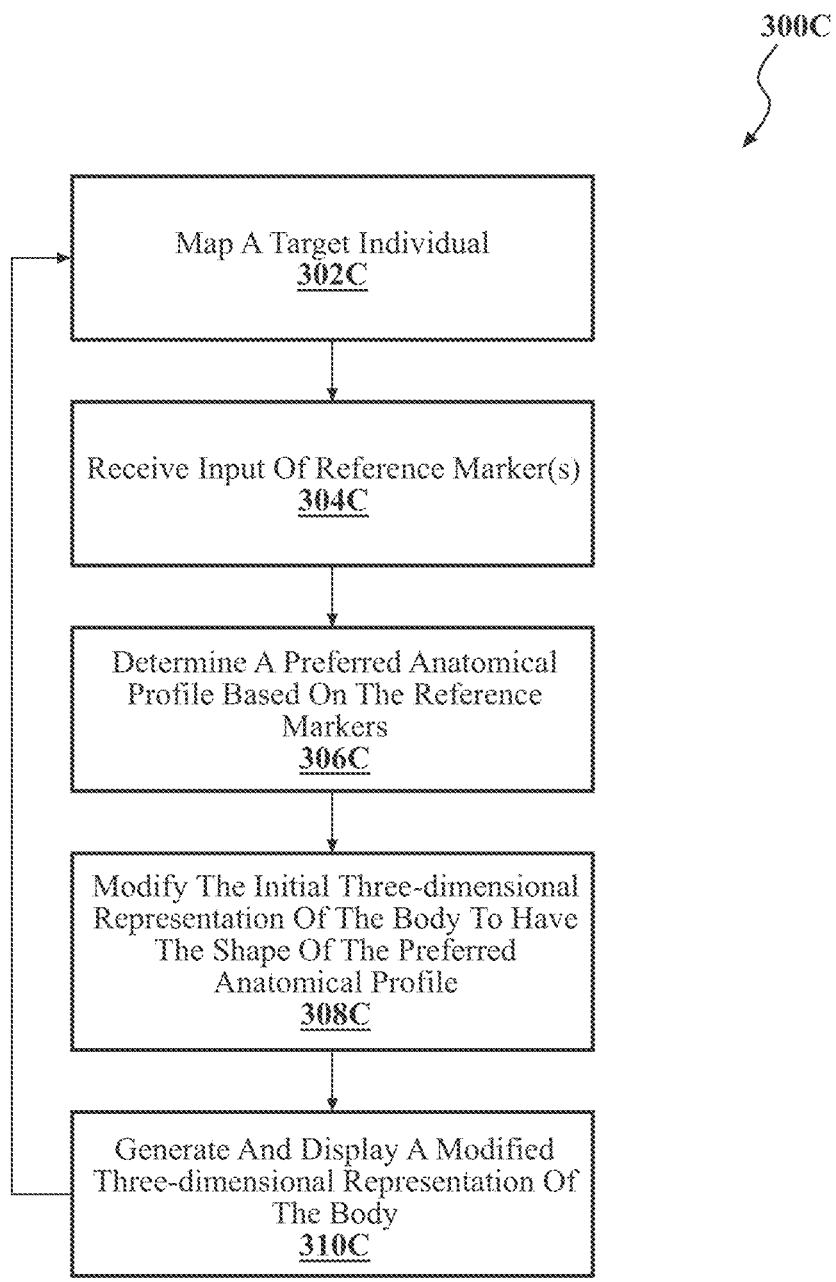
FIG. 3C is a block diagram illustrating an exemplary method for displaying a three-dimensional depiction of a patient having a body of a preferred anatomical profile.

FIG. 3C is a flow chart illustrating a method 300C for displaying a visual three-dimensional depiction of a patient having a body of a preferred anatomical profile. According to one example, the method 300C may be performed by an electronic device, such as the augmented reality device 102. The method 300C begins at block 302C where the augmented reality device maps a target individual (e.g., target individual 106) so as to generate an initial three-dimensional representation of the body. The target individual has a body. For example, at block 302, the image capture device 108a, 108b may detect the target individual 106 via the detection module 210 and/or the tracking module 212.

At block 304C, the method includes identifying a plurality of reference markers (e.g., reference markers 112) on the visual representation (e.g., the visual representation 105, 105') of the body. For example, the augmented reality device 102 may receive the reference markers 112 from the user's interaction with the display 110a, 110b, machine learning, or another previously-described method. In some implementations, the augmented reality device 102 may receive an input of reference markers 112 from the user 104 and receive and generate the graphical representation 113 from the augmented reality module 204.

At block 306C, the method includes determining, at a processor, a preferred anatomical profile (e.g., anatomical profile 216) of the target individual based on the plurality of reference markers, the preferred anatomical profile being a preferred three-dimensional representation of the body that is a body of a fit or healthy person. The anatomical profile may include a plurality of characteristics (e.g., age, gender, etc.) corresponding to the target individual. In some implementations, the augmented reality device 102 receives a preferred anatomical profile based on the reference markers 112. For example, the anatomy module 216 may transmit the preferred anatomical profile to the augmented reality device 102 through the augmented reality module 204.

At block 308C, the method includes modifying, in three dimensions, the initial three-dimensional representation 113' of the body so as to have a shape of the preferred anatomical profile. At block 310C, the method includes the step of displaying the modified initial three-dimensional representation of the body. As such, the patient can see what they would actually look like if their body were adjusted to the preferred anatomical profile. The resulting image is it is not just a preferred profile overlaid onto the patient, but it is the patient's body shape that is modified.

FIG. 4 is schematic view of an example computing device 400 that may be used to implement the systems and methods described in this document. The computing device 400 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 400 includes a processor 410, memory 420, a storage device 430, a high-speed interface/controller 440 connecting to the memory 420 and high-speed expansion ports 450, and a low speed interface/controller 460 connecting to a low speed bus 470 and a storage device 430. Each of the components 410, 420, 430, 440, 450, and 460, are interconnected using various busses, and may be mounted on a common motherboard or in other manners as appropriate. The processor 410 can process instructions for execution within the computing device 400, including instructions stored in the memory 420 or on the storage device 430 to display graphical information for a graphical user interface (GUI) on an external input/output device, such as display 480 coupled to high speed interface 440. In other implementations, multiple processors and/or multiple buses may be used, as appropriate, along with multiple memories and types of memory. Also, multiple computing devices 400 may be connected, with each device providing portions of the necessary operations (e.g., as a server bank, a group of blade servers, or a multi-processor system).

The memory 420 stores information non-transitorily within the computing device 400. The memory 420 may be a computer-readable medium, a volatile memory unit(s), or non-volatile memory unit(s). The non-transitory memory 420 may be physical devices used to store programs (e.g., sequences of instructions) or data (e.g., program state information) on a temporary or permanent basis for use by the computing device 400. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 430 is capable of providing mass storage for the computing device 400. In some implementations, the storage device 430 is a computer-readable medium. In various different implementations, the storage device 430 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 420, the storage device 430, or memory on processor 410.

The high speed controller 440 manages bandwidth-intensive operations for the computing device 400, while the low speed controller 460 manages lower bandwidth-intensive operations. Such allocation of duties is exemplary only. In some implementations, the high-speed controller 440 is coupled to the memory 420, the display 480 (e.g., through a graphics processor or accelerator), and to the high-speed expansion ports 450, which may accept various expansion cards (not shown). In some implementations, the low-speed controller 460 is coupled to the storage device 430 and a low-speed expansion port 490. The low-speed expansion port 490, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 400 may be implemented in a number of different forms, as shown in the figure. For example, it may be implemented as a standard server 400a or multiple times in a group of such servers 400a, as a laptop computer 400b, or as part of a rack server system 400c.

Among other advantages, the present disclosure provides methods, user devices, and systems for displaying augmented anatomical features. An augmented reality device may overlay virtual images of anatomy on top of the human body illustrate an approximation of the structures, tissues or organs that lie beneath the surface of an individual, such as a target individual, in front of a user, such as a healthcare professional. The virtual images can be adjusted to fit the target individual. The user may use the augmented reality device to identify certain anatomical reference points on the body of the target individual, and use those points to anchor and adjust the virtual images over the target individual. The virtual images may be representative of human anatomy of a human of similar age, sex, etc.

Among other advantages, the present disclosure also provides a method, user device, and system that does not require input of data files from outside imaging (e.g., x-ray, magnetic resonance imaging, computed tomography scan, etc.). Such files may have incompatible formats, be large and unwieldy, or require a large amount of processing power for each target individual.

Among other advantages, the present disclosure also provides a method, user device, and system that may be for general use. In this regard, use of the augmented reality device may not be restricted to certified healthcare providers. Furthermore, the expectation of the augmented reality device may be to output or display a computer-generated approximation of a representative human anatomy.

Among other advantages, the present disclosure also provides broad applicability. The augmented reality device may be in constant and rapid use with one target individual after another, and without requiring the input of outside data.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

A number of implementations have been described. Nevertheless, it will be understood that various modifications may be made without departing from the spirit and scope of the disclosure. Accordingly, other implementations are within the scope of the following claims.

What is claimed is:

1. A method comprising:
    positioning, based on a set of gestures from a user captured within an environment of a target individual, a set of reference markers relative to the target individual, wherein:
        each gesture of the set of gestures corresponds to a body part of the target individual, and
        the set of gestures are captured by an image capture device of a wearable augmented reality device;
    displaying each reference marker of the set of reference markers over the body part associated with the corresponding gesture via the wearable augmented reality device;
    determining, at a processor, an anatomical profile of the target individual based on an input from the user, wherein the anatomical profile includes an anatomical feature;
    determining a location for the anatomical feature based on the set of reference markers; and
    displaying a graphical representation of the anatomical feature at the location via the wearable augmented reality device.

2. The method of claim 1, wherein the set of gestures includes a set of hand gestures from the user.

3. The method of claim 1, wherein the wearable augmented reality device includes a headset or glasses.

4. The method of claim 1, wherein the set of reference markers correspond to at least one of a navel, a portion of a sternum, a portion of a hip, a portion of a collarbone, or a portion of a shoulder.

5. The method of claim 1, wherein the anatomical feature includes at least one of: organs, bones, muscles, body fat, or blood vessels.

6. The method of claim 1, further comprising determining a distance between a first reference marker of the set of reference markers and a second reference marker of the set of reference markers, wherein the anatomical feature corresponds to the distance between the first reference marker and the second reference marker.

7. The method of claim 1, wherein the wearable augmented reality device includes:
    an image capture device configured to capture the set of gestures from the user; and
    one or more lenses configured to display the set of reference markers and the graphical representation of the anatomical feature.

8. The method of claim 7, wherein a user interface menu is displayed to the user via the one or more lenses.

9. The method of claim 1, wherein:
    the graphical representation of the anatomical feature represents a set of estimated anatomical features of the target individual; and
    the set of estimated anatomical features includes a set of inner anatomical features for a human body sized to the target individual using the set of reference markers.

10. The method of claim 1, further comprising:
    modifying, at the processor, the anatomical feature; and
    displaying to the user a graphical representation of the modified anatomical feature.

11. A system comprising:
    a wearable augmented reality device including one or more lenses and an image capture device;
    data processing hardware in communication with the one or more lenses and the image capture device; and
    memory hardware in communication with the data processing hardware, the memory hardware storing instructions that when executed on the data processing hardware cause the data processing hardware to perform operations including:
        positioning, based on a set of gestures from a user captured within an environment of a target individual, a set of reference markers relative to the target individual, wherein:
            each gesture of the set of gestures corresponds to a body part of the target individual, and
            the set of gestures are captured by the image capture device of a wearable augmented reality device;
        displaying each reference marker of the set of reference markers over the body part associated with the corresponding gesture via the one or more lenses;
        determining, at a processor, an anatomical profile of the target individual based on the set of reference markers, wherein the anatomical profile includes an anatomical feature;
        determining a location for the anatomical feature based on the set of reference markers; and
        displaying a graphical representation of the anatomical feature at the location via the one or more lenses.

12. The system of claim 11, wherein the set of gestures includes a set of hand gestures from the user.

13. The system of claim 11, wherein the wearable augmented reality device includes one of a headset or glasses.

14. The system of claim 11, wherein the set of reference markers correspond to at least one of a navel, a portion of a sternum, a portion of a hip, a portion of a collarbone, or a portion of a shoulder.

15. The system of claim 11, wherein the anatomical feature includes at least one of organs, bones, muscles, body fat, or blood vessels.

16. The system of claim 11, wherein the operations further comprise determining a distance between a first reference marker of the set of reference markers and a second reference marker of the set of reference markers, wherein at least one anatomical feature of the anatomical feature corresponds to the distance between the first reference marker and the second reference marker.

17. The system of claim 11, wherein a user interface menu is displayed to the user via the one or more lenses.

18. The system of claim 11, wherein:
- the graphical representation of the anatomical feature represents a set of estimated anatomical features of the target individual; and
- the set of estimated anatomical features includes a set of inner anatomical features for a human body sized to the target individual using the set of reference markers.

19. The system of claim 11, wherein the operations further comprise:
- modifying the anatomical feature; and
- displaying to the user a graphical representation of the modified anatomical feature via the one or more lenses.

* * * * *